United States Patent
Johnson et al.

(10) Patent No.: US 8,987,308 B2
(45) Date of Patent: Mar. 24, 2015

(54) **COMPOUNDS FOR THE TREATMENT OF *CLOSTRIDIUM DIFFICILE*-ASSOCIATED DISEASE**

(71) Applicant: Summit Corporation Plc, Abingdon Oxfordshire (GB)

(72) Inventors: Peter David Johnson, Abingdon Oxfordshire (GB); Richard John Vickers, Abingdon Oxfordshire (GB); Francis Xavier Wilson, Abingdon Oxfordshire (GB); Colin Richard Dorgan, Abingdon Oxfordshire (GB); Lauren Jayne Sudlow, Abingdon Oxfordshire (GB); Stephen Paul Wren, Abingdon Oxfordshire (GB); Renate van Well, Abingdon Oxfordshire (GB)

(73) Assignee: Summit Corporation Plc, Abingdon (GB)

( * ) Notice: Subject to any disclaimer, the term of this patent is extended or adjusted under 35 U.S.C. 154(b) by 0 days.

(21) Appl. No.: 13/691,319

(22) Filed: Nov. 30, 2012

(65) Prior Publication Data
US 2013/0095057 A1    Apr. 18, 2013
US 2013/0309191 A9    Nov. 21, 2013

Related U.S. Application Data

(63) Continuation of application No. PCT/GB2011/000831, filed on Jun. 1, 2011.

(30) Foreign Application Priority Data

Jun. 1, 2010 (GB) .................................. 1009097.5
Apr. 27, 2011 (GB) .................................. 1106981.2

(51) Int. Cl.
| | | |
|---|---|---|
| C07D 401/04 | (2006.01) |
| A61K 31/44 | (2006.01) |
| C07D 401/14 | (2006.01) |
| A61K 31/424 | (2006.01) |
| A61K 31/546 | (2006.01) |
| A61K 38/14 | (2006.01) |
| A61K 45/06 | (2006.01) |
| C07D 405/14 | (2006.01) |
| C07D 409/14 | (2006.01) |
| C07D 471/04 | (2006.01) |
| C07D 495/04 | (2006.01) |
| A61K 31/4439 | (2006.01) |
| C07D 403/14 | (2006.01) |
| C07D 417/14 | (2006.01) |
| A61K 31/4164 | (2006.01) |
| A61K 31/4365 | (2006.01) |
| A61K 31/437 | (2006.01) |
| A61K 31/74 | (2006.01) |
| A61K 36/064 | (2006.01) |
| A61K 39/395 | (2006.01) |

(52) U.S. Cl.
CPC ........... *C07D 401/14* (2013.01); *A61K 31/424* (2013.01); *A61K 31/546* (2013.01); *A61K 35/741* (2013.01); *A61K 38/14* (2013.01); *A61K 45/06* (2013.01); *C07D 401/04* (2013.01); *C07D 405/14* (2013.01); *C07D 409/14* (2013.01); *C07D 471/04* (2013.01); *C07D 495/04* (2013.01); *A61K 31/4439* (2013.01); *C07D 403/14* (2013.01); *C07D 417/14* (2013.01); *A61K 31/4164* (2013.01); *A61K 31/4365* (2013.01); *A61K 31/437* (2013.01); *A61K 31/74* (2013.01); *A61K 35/747* (2013.01); *A61K 36/064* (2013.01); *A61K 39/395* (2013.01)
USPC ........ 514/339; 514/365; 514/372; 546/268.1; 546/273.4; 548/146; 548/206

(58) Field of Classification Search
None
See application file for complete search history.

(56) References Cited

U.S. PATENT DOCUMENTS

| | | | |
|---|---|---|---|
| 3,503,929 | A | 3/1970 | Loudas |
| 3,661,849 | A | 5/1972 | Culbertson |
| 4,087,409 | A | 5/1978 | Preston |
| 5,089,592 | A | 2/1992 | Schrock et al. |
| 5,317,078 | A | 5/1994 | Connell et al. |

(Continued)

FOREIGN PATENT DOCUMENTS

| | | |
|---|---|---|
| CN | 1164227 A | 11/1997 |
| EP | 0 511 187 A1 | 3/1992 |

(Continued)

OTHER PUBLICATIONS

Wu et al., Toxicology, 236, pp. 1-6, 2007.*

(Continued)

*Primary Examiner* — Zinna Northington Davis
(74) *Attorney, Agent, or Firm* — Wolf, Greenfield & Sacks, P.C.

(57) ABSTRACT

Disclosed are compounds of formula (I):

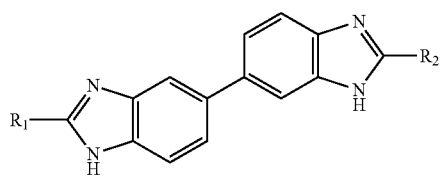

or a pharmaceutically acceptable N-oxide, salt, hydrate, solvate, complex, bioisostere, metabolite or prodrug thereof, which are of use in the treatment of infection with, and diseases caused by, *Clostridium difficile*.

15 Claims, No Drawings

(56) References Cited

U.S. PATENT DOCUMENTS

| | | | |
|---|---|---|---|
| 5,824,698 | A | 10/1998 | Hasler et al. |
| 2006/0036061 | A1 | 2/2006 | Shin et al. |
| 2007/0112048 | A1 | 5/2007 | Bavari et al. |
| 2010/0033088 | A1 | 2/2010 | Hwang et al. |
| 2010/0305118 | A1 | 12/2010 | Clark et al. |
| 2010/0316649 | A1 | 12/2010 | Zhang et al. |
| 2012/0020950 | A1 | 1/2012 | Davis et al. |

FOREIGN PATENT DOCUMENTS

| | | |
|---|---|---|
| EP | 1 547 996 A1 | 6/2005 |
| JP | 50-140445 A2 | 11/1975 |
| JP | 50154250 A | 12/1975 |
| JP | 3-500661 T2 | 2/1991 |
| JP | 11158158 A | 6/1999 |
| JP | 2000-95767 A2 | 4/2000 |
| JP | 2005-500980 A | 1/2005 |
| JP | 2007-509041 A | 4/2007 |
| WO | WO 96/16042 A1 | 5/1996 |
| WO | WO 00/63180 A1 | 10/2000 |
| WO | WO 01/32219 A2 | 5/2001 |
| WO | WO 02/42281 A1 | 5/2002 |
| WO | WO 02/055045 A1 | 7/2002 |
| WO | WO 02/060374 A2 | 8/2002 |
| WO | WO 02/060879 A2 | 8/2002 |
| WO | WO 03/007955 A2 | 1/2003 |
| WO | WO 03/035065 A1 | 5/2003 |
| WO | WO 03/105846 A1 | 12/2003 |
| WO | WO 2004/001058 A2 | 12/2003 |
| WO | WO 2004/041209 A2 | 5/2004 |
| WO | WO 2006/052913 A1 | 5/2006 |
| WO | WO 2006/076009 A2 | 7/2006 |
| WO | WO 2006/077412 A1 | 7/2006 |
| WO | WO 2007/056330 A1 | 5/2007 |
| WO | WO 2007/114652 A1 | 10/2007 |
| WO | WO 2007/148093 A1 | 12/2007 |
| WO | WO 2008/025821 A1 | 3/2008 |
| WO | WO 2008/048991 A2 | 4/2008 |
| WO | WO 2008/073451 A1 | 6/2008 |
| WO | WO 2008/075196 A1 | 6/2008 |
| WO | WO 2009/147189 A1 | 12/2009 |
| WO | WO 2010/017401 A1 | 2/2010 |
| WO | WO 2010/063996 A2 | 6/2010 |
| WO | WO 2010/099527 A1 | 9/2010 |
| WO | WO 2010/112874 A1 | 10/2010 |
| WO | WO 2010/138791 A1 | 12/2010 |
| WO | WO 2011/046954 A1 | 4/2011 |

OTHER PUBLICATIONS

Yin et al, Inorganic Chemistry (2007), 46(17), 6891-6901.*
Yin et al, Synthetic Metals, 154 (2005) pp. 233-236.*
Abubakar et al., Health Technology Assessment, Sep. 2007, vol. 11, No. 36, Chapter 2, pp. 3-10.
[No Author Listed], 1H-benzimidazole, 5,5'-methylenebis[2-(4-piperidinyl)-(9CI) (CA Index Name). Chemical Library. Sep. 13, 2002. Abstract. XP-002567962.
[No Author Listed], Phemol, 2,2'-[5,5'-bi-1H-benzimidazole]-2,2'-diybis[4-amino-9CI)] (CA Index Name). Chemical Library. May 22, 2003. Abstract. XP-002567963.
Akashi, Reactions and applications of itaconic acid. XV. Synehesis of heat resistant polymers from the reaction products between itaconci acid and two aromatic diamines. Memoirs of the faculty of engineering. Kobe University 1970;16:162-174. Abstract.
Bailly et al., Mode of DNA binding of bis-benzimidazoles and related structures studied by electric linear dichroism. J Biomol Struct Dyn. Aug. 1994;12(1):173-81.
Beerman et al., Effects of analogs of the DNA minor groove binder Hoechst 33258 on topoisomerase II and I mediated activities. Biochim Biophys Acta. May 7, 1992;1131(1):53-61.
Bowser et al., Novel anti-infection agents: small-molecule inhibitors of bacterial transcription factors. Bioorg Med Chem Lett. Oct. 15, 2007;17(20):5652-5. Epub Aug. 21, 2007.
Brand et al., Oligomeric benzimidazoles with reactive end groups. Journal of Polymer Science: Polymer Chemistry Edition. 1979;174(4):1145-1152.
Chaudhuri et al., An experimental and computational analysis on the differential role of the positional isomers of symmetric bis-2-(pyridyl)-1H-benzimidazoles as DNA binding agents. J Org Chem. Mar. 16, 2007;72(6):1912-23. Epub Feb. 17, 2007.
Clark et al., Designer DNA-binding drugs: the crystal structure of a meta-hydroxy analogue of Hoechst 33258 bound to d(CGCGAAT-TCGCG)2. Nucleic Acids Res. Dec. 15, 1996;24(24):4882-9.
Guiles et al., New agents for *Clostridium* difficile-associated disease. Expert Opin Investig Drugs. Nov. 2008;17(11):1671-83.
Hao et al., Convenient synthesis of 2-arylbenzimidazoles and 2,2'-diaryl-bisbenzimidazoles. Synthetic Communications, 2003;33(1):79-86.
Kane et al., Polymorphism in 2,2'-diphenyl-5,5'-bibenzimidazole. Journal of Heterocyclic Chemistry, 1970;7:943-6.
Le Sann et al., New mustard-linked 2-aryl-bis-benzimidazoles with anti-proliferative activity. Org Biomol Chem. Apr. 7, 2006;4(7):1305-12. Epub Mar. 9, 2006.
Leffler et al., Treatment of *Clostridium* difficile-associated disease. Gastroenterology. May 2009;136(6):1899-912. Epub May 7, 2009.
Niume et al., Polybenzimidazoles containing anthracene photodimer. Journal of Polymer Science, Polymer Chemistry Edition. 1982;20:663-673.
Rigault et al., Lnathanide-assisted self-assembly of an inert, metal-containing nonadentate tripodal receptor. Angew. Chem. Int. Ed. 1998;37(1/2):169-172.
Samsoniya et al., Bisindole 39. Synthesis of the new derivatives of bis (1H-indolo-5-yl) methane. Sakartvelos Mecnierebeta Akademiis Macne. Kimiis Seria 2003;29(3-4):222-224. Abstract.
Srivastava et al., Studies in antiparasitic agents. Part 20. Synthesis of probenzimidazoles, benzimidazoles and pyrimidio (1,2-a) benzimidazoles as possible anthelmintics. Indian Journal of Chemistry, Section B. 1993; 32B(10):1035-1044. Abstract.
Yin et al., Efficient synthesis and characterization of novel bibenzimidazole oligomers and polymers as potential conjugated chelating ligands. J Org Chem. Nov. 11, 2005;70(23):9436-46.
Yokota et al., Evaluation of the thermal stability of high polymers by thermogravimetry. Poly(benzimidazole) and its model compounds. Kobunshi Kagaku 1972;29(6):428-31. Abstract.
Chauvin et al., *A Polyoxyethylene-Substituted Bimetallic Europium Helicate for Luminescent Staining of Living Cells*, Chem. Eur. J. 2007, 13:9515-26.
Souillac et al., *Characterization of Delivery Systems, Differential Scanning Calorimetry*, Encyclopedia of Controlled Drug Delivery, 1999, 212-227, John Wiley & Sons.
Vippagunta et al., *Crystalline Solids*, Advanced Drug Delivery Reviews 2001, 48:3-26.
International Preliminary Report on Patentability mailed Dec. 13, 2012 for Application No. PCT/GB2011/000831.
[No Author Listed] Caplus Accession No. 1960:135340. May 2, 1959. 1 page.
Hori et al., Synthetic Inhibitors of the Processing of Pretransfer RNA by the Ribonuclease P Ribozyme: Enzyme Inhibitors Which Act by Binding to Substrate. Biochem. Jan. 23, 2001;40(3):603-8.
Org Biomol Chem. Apr. 7, 2006;4(7):1305-12. Epub Mar. 9, 2006.
Office Communication mailed May 23, 2014 for U.S. Appl. No. 13/131,469.
[No Author Listed], *Clostridium difficile* Associated Disease (CDAD) Fact Sheet For Patients. Ottawa Hospital. Ontario, Canada. 2012. 2 pages.
Evans et al., Co-crystal Structure of REP3123 Bound to *Clostridium difficile* Methionyl tRNA Synthetase. 47th International Conference of Antimicrobial Agents. ICAAC. Poster No. F1-2114. 2007.
Guiles et al., Novel Inhibitors of Methionyl tRNA Synthetase from *Clostridium difficile*: Identification and Synthesis of REP3123. 47th International Conference of Antimicrobial Agents. ICAAC. Poster No. F1-2112. 2007.
Huang et al., The Challenge of Antibacterial Drug Development: Integrating Chemistry and Biology. Trip Report. Cambridge Healthtech Institute's 2nd Annual Meeting. San Diego, CA. Apr. 23-4, 2008. Technical Reports. 13 pages.

(56) References Cited

OTHER PUBLICATIONS

Kuijper et al., Emergence of *Clostridium difficile*-associated disease in North America and Europe. Eur Soc Clin Microbiol Infect Dis. 2006;12(6):2-18. Review.

McNulty et al., Successful control of *Clostridium difficile* infection in an elderly care unit through use of a restrictive antibiotic policy. J Antimicrob Chemother. 1997;40:707-11.

O'Connor et al., Antibiotic prescribing policy and *Clostridium difficile* diarrhoea. Q J Med. 2004;97:423-9. doi:10.1093/qjmed/hch076.

Bhattacharya et al., Metal-ion-mediated tuning of duplex DNA binding by bis(2-(2-pyridy1)-1H-benzimidazole). Chem Asian J. May 4, 2007;2(5):648-55.

Singh et al., Synthetic Utility of Catalytic Fe(III)/Fe(II) Redox Cycling Towards Fused Heterocycles: A Facile Access to Substituted Benzimidazole, Bisbenzimidazole and Imidazopyridine Derivatives. Synthesis. 2000;(10):1380-90.

* cited by examiner

COMPOUNDS FOR THE TREATMENT OF *CLOSTRIDIUM DIFFICILE*-ASSOCIATED DISEASE

This application is a continuation of and claims the benefit under 35 U.S.C. §120 and §365(c) of International Application No. PCT/GB2011/000831, with an international filing date of Jun. 1, 2011, and entitled "Compounds for the Treatment of *Clostridium Difficile* Associated Disease", the entire contents of which are herein incorporated by reference. This application also claims the benefit of Great Britain Patent Application No. 1009097.5 filed on Jun. 1, 2010 and Great Britain Patent Application No. 1106981.2 filed on Apr. 27, 2011, the entire contents of each of which are herein incorporated by reference.

FIELD OF THE INVENTION

The present invention relates to compounds which are of use in the treatment of infection with, and diseases caused by, *Clostridium difficile*, to compositions containing these compounds and to methods of treating *Clostridium difficile*-associated diseases (CDAD) using the compounds.

BACKGROUND TO THE INVENTION

Antibacterial Drugs and *Clostridium difficile*

The development of antibacterial drugs represents one of the most important medical advances of the 20$^{th}$ Century. Previously untreatable diseases could now be readily controlled and it was felt that many diseases would be eradicated with these new wonder drugs. Despite these significant advances in treatment, infectious diseases are the third major cause of mortality in the USA (Clin. Infect. Dis., 2004, 38, 1279-1286) and remain one of the most significant global healthcare problems. Rates of resistance in all of the major pathogenic bacteria are rising dramatically and of particular concern is the increasing number and severity of nosocomial infections (Infectious Disease Society of America, 2004, *Bad Bugs, No Drugs*). The emergence of multi-drug resistant pathogens has rendered many of the current frontline drugs completely ineffective in controlling many diseases.

A particular subset of bacterial pathogens of concern is those classified as spore-forming bacteria. Bacterial spores (endospores) are dormant, non-reproductive structures formed by bacteria in response to environmental stress. Once environmental conditions become favourable, the spores germinate and the bacteria proliferate. In the case of pathogenic bacteria, germination in a human host may result in disease.

Bacterial spores are extremely tolerant to many agents and environmental conditions including radiation, desiccation, temperature, starvation and chemical agents, This natural tolerance to chemical agents allows spores to persistent for many months in key environments such as hospitals, other healthcare centres and food production facilities, where standard cleaning agents, germicides and sterilisation processes do not eradicate the bacteria. In the case of food production, the presence of spores can have significant consequences ranging from simple food spoilage through to the spread of food-borne pathogens and food poisoning. More recently, attention has been drawn to the risks associated with the spores of *Bacillus anthracis*, the causative agent of anthrax. The spores can be readily prepared as a dry powder that can be disseminated by numerous methods and used as a bioterrorist agent. Anthrax is considered the single most worrying bioterrorism agent (CDC Emerg, Infect. Dis., 2004, 5 (4), 552-555). This can be highlighted by the postal anthrax attacks in the United States in 2001. There were 22 confirmed infections resulting in 5 deaths with the cost of cleanup and decontamination following the attacks estimated at $1 billion.

Important spore-forming bacteria are the Gram-positive endospore-forming bacteria of the genera *Bacillus* and *Clostridium*, Examples of the genus *Bacillus* of health concern to humans include, but are not limited to, *B. anthracis* and *B. cereus*. *Bacillus* anthracis is of particular concern as the causative agent of anthrax. Anthrax infection can occur through ingestion, inhalation or cutaneous contact with *Bacillus anthracis* spores resulting in three distinct clinical forms. Cutaneous infection accounts for about 95% of all infections and is generally well controlled with the use of suitable antibiotics. Around 20% of untreated cases of cutaneous anthrax will result in death. Intestinal infection is characterized by an acute inflammation of the intestinal tract resulting in nausea, loss of appetite, vomiting, fever, abdominal pain, vomiting of blood and severe diarrhoea. Intestinal anthrax results in death in 25% to 60% of cases. The most severe form of the disease is pulmonary anthrax which is often fatal, even with aggressive and timely antibiotic administration. The ability to readily disperse anthrax spores through the air and over a wide area to induce pulmonary anthrax makes anthrax the primary bioterrorism agent.

Members of the genus *Clostridium* are Gram-positive, spore-forming, obligate anaerobes. Example species causing human disease include, but are not limited to, *C. perfringens, C. tetani, C. botulinium, C. sordellil* and *C. difficile*. *Clostridial* species are associated with diverse human diseases including tetanus, gas gangrene, botulism and pseudomembraneous colitis and can be a causative agent in food poisoning.

Of particular concern is disease caused by *Clostridium difficile*. *Clostridium difficile* causes *Clostridium difficile*-associated diseases (CDAD) and there has been a ten-fold increase in the number of cases within the last 10 years, with hyper-virulent and drug resistant strains now becoming endemic. Recent HPA figures show there were 55,681 cases of *C. difficile* infection in patients aged 65 years and above in England in 2006 (up 8% on the previous year). Perhaps most worrying are the cases of CDAD with no underlying antibiotic use now being reported.

*Clostridium difficile* is a commensal enteric bacterium, the levels of which are kept in check by the normal gut flora. However, the bacterium is the causative agent of *C. difficile*-associated disease (CDAD) and has been identified as the primary cause of the most serious manifestation of CDAD, pseudomembraneous colitis. CDAD is associated with a wide range of symptoms ranging from mild diarrhoea through to pseudomembraneous colitis, toxic megacolon and death. The primary risk factor for the development of CDAD is the use of antibiotics disrupting the normal enteric bacterial flora causing an overgrowth of *Clostridium difficile*. Although clindamycin is the major antibiotic associated with CDAD, the disease is now associated with nearly all antibiotics including members of the fluoroquinolone, cephalosporin, macrolide, β-lactam and many others classes.

CDAD is primarily of concern in the hospital setting and is of particular concern amongst elderly patients where mortality rates are particularly high. Reported rates of CDAD have increased dramatically in recent years with over 55,000 cases reported in the UK in 2006 (Health Protection Agency Surveillance of Healthcare Associated Infections Report 2007).

Mortality rates in the USA have risen from 5.7 per million of population in 1999 to 23.7 per million in 2004. Colonisation rates of *C. difficile* in the general population are up to 3% although hospitalisation dramatically increases the rates of colonisation up to 25%. Of particular concern is the emergence of new endemic strains. A particularly pertinent example is the hyper-virulent BI/NAP1 (also known as ribotype 027) strain which shows increased toxin A and B production as well as the production of additional novel binary toxins.

A critical factor associated with clostridial species is the high rates of bacterial spores present in hospital environments. It has recently been shown that many of the standard hospital cleaning agents in use are ineffective at eradicating clostridial spores for the environment resulting in ineffective disease control (Infect Cont. Hosp. Epidemiol., 2007, 28, 920-5). The hyper-sporulation characteristics of strains such as BI/NAP1 contribute significantly to the issue.

Although the primary risk factors associated with CDAD are underlying antibiotic use and age (CMAJ, 2008, 179 (8), 767-772; J. Antimicrob. Chem., 2003, 51, 1339-1350) there are numerous other associated factors including for example the use of proton pump inhibitors, use of H2 receptor antagonists, use of diuretics, length of hospital stay, use of feeding tubes, mechanical ventilation and underlying co-morbidity.

Gastric acidity is part of the natural defence mechanism against ingested pathogens and any reduction in the acidity of the stomach can result in colonisation of the normally sterile upper gastrointestinal tract which can result in a disturbance of the normal enteric microflora. As such, the use of gastric acid suppressive agents, such as proton pump inhibitors (PPIs) and histamine H2-receptor antagonists (H2Ras) is associated with an increased risk of *C. difficile* colonisation and subsequent development of CDAD. The use of PPIs and H2Ras has previously been associated with other enteric infections such as traveller's diarrhoea, salmonellosis and cholera. Dial et al. have reported that the risk of CDAD increases with the use of gastric acid suppressive agents in both the community (JAMA, 2005, 294(23), 2989-2995) and hospital settings (CMAJ, 2004, 171(1), 33-38).

PPIs include, but are not limited to, omeprazole (Losec, Prilosec, Zegerid), lansoprazole (Prevacid, Zoton, Inhibitol), esomeprazole (Nexium), pantoprazole (Protonix, Somac, Pantoloc, Pantozol, Zurcal, Pan) and rabeprazole (Rabecid, Aciphex, Pariet, Rabeloc).

H2Ras include, but are not limited to, cimetidine (Tagamet), ranitidine (Zinetac, Zantac), famotidine, (Pepcidine, Pepcid), roxatidine (Roxit) and nizatidine (Tazac, Axid).

Triple therapy with PPIs or H2Ras together with a combination of two antibiotics is a recognised treatment for the eradication of *Helicobacter pylori* infections (Aliment. Pharmacol. Ther., 2001, 15(5), 613-624, Helicobacter., 2005, 10(3), 157-171). However, there are a few reports that this triple therapy regimen can lead to CDAD side effects (Am. J, Gastroenterol., 1998, 93(7), 1175-1176; J. Int, Med., 1998, 243(3), 251-253; Aliment. Pharm. Ther., 2001, 15(9), 1445-1452; Med, Sci. Monit., 2001, 7(4), 751-754). Typical antibacterials used to treat *Helicobacter pylori* infections are a combination of agents selected from, but not limited to metronidazole, amoxicillin, levofloxacin and clarithromycin—many of which are strongly associated with the development of CDAD. Current therapies are extremely limited; particularly in view of the fact nearly all antibiotic classes are associated with causing the disease. The only FDA approved drug for treatment of CDAD is vancomycin although metronidazole is also extensively used. Widespread vancomycin use for the treatment of CDAD is of concern due to its bacteriostatic action against clostridia, relatively high cost and the possible selection of resistant *C. difficile* strains as well as other bacteria (particularly *Enterococcus* spp.). A key issue with both metronidazole and vancomycin is the high relapse rate with at least 20% of patients experiencing at least one recurrent episode. Relapse is proposed to occur due to the inability to eradicate the clostridium spores during therapy resulting in subsequent outgrowth to a pathogenic state. This inability to control spore formation allows for continued contamination of the hospital environment. As such, agents able to eradicate vegetative cells and control endospores would be of significant advantage.

The primary therapy option for the treatment of CDAD is discontinuation of any current antimicrobial treatment followed by appropriate use of either vancomycin or metronidazole. Both agents are usually administered orally although metronidazole may also be administered intravenously and in severe cases, vancomycin may also be administered via numerous other routes including intracolonic, through nasal gastric tube or as a vancomycin-retention enema. Additional antibiotics agents that have been reported to be used in the treatment of CDAD include fusidic acid, rifamycin and its analogues, teicoplanin and bacitracin although none show particular efficacy over vancomycin or metronidazole. In addition to halting any offending antibacterial treatment, the use of antiperistaltic agents, opiates, or loperamide should be avoided since they can reduce clearance of the *C. difficile* toxins and exacerbate toxin-mediated colonic injury. Such agents may also precipitate ileus and cause toxic dilation of the colon (J. Med. Microbiol., 2005, 54, 101-111; JAMA, 1993, 269, 71-5; Postgrad. Med. J., 1990, 66(777), 582).

Alternative therapies, used as standard alone agents or in conjunction with antibacterials, are aimed at either trying to re-establish the native gut microorganism population, reducing the levels of *C. difficile* toxins or stimulating the immune system (for reviews see Antibiotic Treatment for *Clostridium difficile*-Associated Diarrhea in Adults, *Cochrane Database of Systematic Reviews* 2007, Issue 3. Art. No.: C0004610.; Clin. Inf. Dis., 2008, 46(S1), S32-S42; Clin. Inf. Dis., 2007, 45(S2), S122-S128; J. Med. Microbiol., 2005, 54, 101-111 and references therein). Thus, alternative CDAD therapies include provision of *Saccharomyces boulardii* or *Lactobacillus acidophilus* in conjunction with antibiotics, faecal transplantation and in severe cases where all other therapy options have failed, surgery. Although rates of colectomy are low (up to 3% of cases) it is associated with high mortality rates (up to 60%).

As such, there is a pressing need for new and effective agents to treat diseases associated with spore forming bacteria, particularly those caused by members of the genera *Clostridium* and *Bacillus* and in particular disease associated with *Clostridium difficile* infection. This need is particularly acute in the light of the refractory nature of *Clostridium difficile* to many broad spectrum antibiotics (including ⊖-lactam and quinolone antibiotics) and the frequency with which resistance emerges (Antimicrob. Agents Chemother., 1985, 28(6): 842-844).

3. Prior Art

WO2007056330, WO2003105846 and WO2002060879 disclose various 2-amino benzimidazoles as antibacterial agents.

WO2007148093 discloses various 2-amino benzothiazoles as antibacterial agents.

WO2006076009, WO2004041209 and Bowser et al. (Bioorg. Med. Chem. Lett 2007, 17, 5652-5655) disclose various substituted benzimidazole compounds useful as anti-infectives that decrease resistance, virulence, or growth of microbes. The compounds are said not to exhibit intrinsic antimicrobial activity in vitro.

U.S. Pat. No. 5,824,698 discloses various dibenzimidazoles as broad-spectrum antibiotics, disclosing activity against both Gram-negative and Gram-positive bacteria, including *Staphylococcus* spp. and *Enterococcus* spp. However, this document does not disclose activity against anaerobic spore-forming bacteria and in particular does not disclose activity against any *Clostridium* spp. (including *C. difficile*).

US 2007/0112048 A1 discloses various bi- and triarylimidazolidines and bi- and triarylamidines as broad-spectrum antibiotics, disclosing activity against both Gram-negative and Gram-positive bacteria, including *Staphylococcus* app., *Enterococcus* spp. and *Clostridium* spp. However, this document does not disclose compounds of general formula (I) as described herein.

Chaudhuri et al. (J. Org. Chem., 2007, 72, 1912-1923) describe various bis-2-(pyridyl)-1H-benzimidazoles (including compounds of formula I as described herein) as DNA binding agents. This document is silent as to potential antibacterial activity,

SUMMARY OF THE INVENTION

Therefore, in a first aspect of the present invention, there is provided a compound of general formula (I):

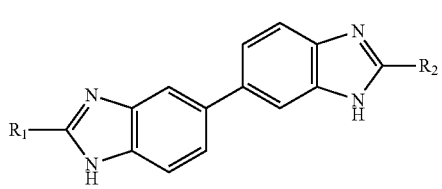

R$^1$ is selected from an optionally substituted aryl, heteroaryl, carbocyclyl and heterocyclyl group, the optional substitution being with one or more substituents selected from halo, CN, NO$_2$, R$^3$, OR$^3$, N(R$^3$)$_2$, COR$^3$, CO$_2$R$^3$, C(=O)SR$^3$, SR$^3$, S(=O)R$^3$, SO$_2$R$^3$, NR$^4$C(=O)R$^3$, NR$^4$CO$_2$R$^3$, OC(=O)NR$^3$R$^4$, NR$^4$SO$_2$R$^3$, C(=NR$^4$)NR$^3$R$^4$, C(=S)NR$^3$R$^4$, NR$^4$C(=NR$^4$)NR$^3$R$^4$, NR$^4$C(=S)NR$^3$R$^4$, NR$^4$C(=O)NR$^3$R$^4$, CONR$^3$R$^4$ and SO$_2$NR$^3$R$^4$;

R$^2$ is an optionally substituted aromatic 8-14 membered fused bicyclic or tricyclic ring system in which one or more of the carbon atoms may be replaced by N, O, S, SO or SO$_2$ and the optional substitution being with one or more substituents selected from halo, CN, NO$_2$, R$^3$, OR$^3$, N(R$^3$)$_2$, COR$^3$, CO$_2$R$^3$, C(=O)SR$^3$, SR$^3$, S(=O)R$^3$, SO$_2$R$^3$, NR$^4$C(=O)R$^3$, NR$^4$CO$_2$R$^3$, OC(=O)NR$^3$R$^4$, NR$^4$SO$_2$R$^3$, C(=NR$^4$)NR$^3$R$^4$, C(=S)NR$^3$R$^4$, NR$^4$C(=NR$^4$)NR$^3$R$^4$, NR$^4$C(=S)NR$^3$R$^4$, NR$^4$C(=O)NR$^3$R$^4$, CONR$^3$R$^4$ and SO$_2$NR$^3$R$^4$;

R$^3$ is selected from H, C$_1$-C$_6$ alkyl, C$_2$-C$_6$ alkenyl, C$_2$-C$_6$ alkynyl, C$_3$-C$_7$ carbocyclyl, C$_4$-C$_7$ heterocyclyl and 5- or 6-membered aryl or heteroaryl, any of which may be optionally substituted with one or more substituents selected from halo, CN, NO$_2$, R$^4$, OR$^4$, N(R$^4$)$_2$, COR$^4$, CO$_2$R$^4$, C(=O)SR$^4$, SR$^4$, S(=O)R$^4$, SO$_2$R$^4$, NR$^4$C(=O)R$^4$, NR$^4$CO$_2$R$^4$, OC(=O)NR$^4$)$_2$, NR$^4$SO$_2$R$^4$, C(=NR$^4$)N(R$^4$)$_2$, C(=S)N(R$^4$)$_2$, NR$^4$C(=NR$^4$)N(R$^4$)$_2$, NR$^4$C(=S)N(R$^4$)$_2$, NR$^4$C(=O)N(R$^4$)$_2$, CON(R$^4$)$_2$ and SO$_2$N(R$^4$)$_2$;

R$^4$ is selected from hydrogen, C$_1$-C$_6$ alkyl and C$_3$-C$_7$ carbocyclyl, optionally substituted with one or more halo atoms;
or a pharmaceutically acceptable N-oxide, salt, hydrate, solvate, complex, bioisostere, metabolite or prodrug thereof, for the treatment of *Clostridium difficile*-associated disease (CDAD).

Certain of the compounds of general formula (I) are novel. Thus, according to the invention, we also provide those compounds of general formula (I) which are novel, together with processes for their preparation, compositions containing them, as well as their use as pharmaceuticals.

Thus, in another aspect, there is provided a compound of general formula I):

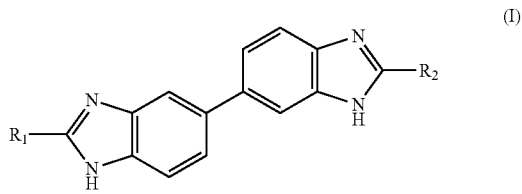

R$^1$ is selected from an optionally substituted aryl, heteroaryl, carbocyclyl and heterocyclyl group, the optional substitution being with one or more substituents selected from halo, CN, NO$_2$, R$^3$, OR$^3$, N(R$^3$)$_2$, COR$^3$, CO$_2$R$^3$, C(=O)SR$^3$, SR$^3$, S(=O)R$^3$, SO$_2$R$^3$, NR$^4$C(=O)R$^3$, NR$^4$CO$_2$R$^3$, OC(=O)NR$^3$R$^4$, NR$^4$SO$_2$R$^3$, C(=NR$^4$)NR$^3$R$^4$, C(=S)NR$^3$R$^4$, NR$^4$C(=NR$^4$)NR$^3$R$^4$, NR$^4$C(=S)NR$^3$R$^4$, NR$^4$C(=O)NR$^3$R$^4$, CONR$^3$R$^4$ and SO$_2$NR$^3$R$^4$;

R$^2$ is an optionally substituted aromatic 8-14 membered fused bicyclic or tricyclic ring system in which one or more of the carbon atoms may be replaced by N, O, S, SO or SO$_2$ and the optional substitution being with one or more substituents selected from halo, CN, NO$_2$, R$^3$, OR$^3$, N(R$^3$)$_2$, COR$^3$, CO$_2$R$^3$, C(=O)SR$^3$, SR$^3$, S(=O)R$^3$, SO$_2$R$^3$, NR$^4$C(=O)R$^3$, NR$^4$CO$_2$R$^3$, OC(=O)NR$^3$R$^4$, NR$^4$SO$_2$R$^3$, C(=NR$^4$)NR$^3$R$^4$, C(=S)NR$^3$R$^4$, NR$^4$C(=NR$^4$)NR$^3$R$^4$, NR$^4$C(=S)NR$^3$R$^4$, NR$^4$C(=O)NR$^3$R$^4$, CONR$^3$R$^4$ and SO$_2$NR$^3$R$^4$;

R$^3$ is selected from H, C$_1$-C$_6$ alkyl, C$_2$-C$_6$ alkenyl, C$_2$-C$_6$ alkynyl, C$_3$-C$_7$ carbocyclyl, C$_4$-C$_7$ heterocyclyl and 5- or 6-membered aryl or heteroaryl, any of which may be optionally substituted with one or more substituents selected from halo, CN, NO$_2$, R$^4$, OR$^4$, N(R$^4$)$_2$, COR$^4$, CO$_2$R$^4$, C(=O)SR$^4$, SR$^4$, S(=O)R$^4$, SO$_2$R$^4$, NR$^4$C(=O)R$^4$, NR$^4$CO$_2$R$^4$, OC(=O)NR$^4$)$_2$, NR$^4$SO$_2$R$^4$, C(=NR$^4$)N(R$^4$)$_2$, C(=S)N(R$^4$)$_2$, NR$^4$C(=NR$^4$)N(R$^4$)$_2$, NR$^4$C(=S)N(R$^4$)$_2$, NR$^4$C(=O)N(R$^4$)$_2$, CON(R$^4$)$_2$ and SO$_2$N(R$^4$)$_2$;

R$^4$ is selected from hydrogen, C$_1$-C$_6$ alkyl and C$_3$-C$_7$ optionally substituted with one or more halo atoms;
or a pharmaceutically acceptable N-oxide, salt, hydrate, solvate, complex, bioisostere, metabolite or prodrug thereof.

The compound as defined above may be for use in therapy or prophylaxis, for example in the treatment of a bacterial infection or disease (for example, in the treatment of CDAD).

In another aspect, there is provided a method of treating a bacterial infection or bacterial disease (for example CDAD) in a subject comprising administering an effective amount of a compound as defined above to said subject.

In another aspect, there is provided a method of killing a bacterium or inhibiting, reducing or preventing the growth thereof, comprising contacting said bacterium with a compound as defined above. In such embodiments the bacterium is preferably *Clostridium difficile*.

Also contemplated are combinations comprising the compound of he invention as defined above with various adjunctive agents as defined below.

Yet other aspects of the invention are defined in the claims set out below.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The phrase "consisting essentially of" is used herein to require the specified integer(s) or steps as well as those which do not materially affect the character or function of the claimed invention.

As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from trauma, injury, surgery, radiological ablation, poisoning or nutritional deficiencies.

As used herein, the term "bacterial disease" refers to any disease that involves (e.g. is caused, exacerbated, associated with or characterized by the presence of) a bacterium residing and/or replicating in the body and/or cells of a subject. The term therefore includes diseases caused or exacerbated by bacterial toxins (which may also be referred to herein as "bacterial intoxication"). The more specific term "Clostridium difficile disease" is to be interpreted accordingly.

As used herein, the term Clostridium difficile-associated disease (CDAD) is used to define any disease that involves (e.g. is caused, exacerbated, associated with or characterized by the presence of) Clostridium difficile residing and/or replicating in the body of a subject. Thus, the term covers any disease, disorder, pathology, symptom, clinical condition or syndrome in which bacteria of the species Clostridium difficile act as aetiological agents or in which infection with one or more strains of Clostridium difficile is implicated, detected or involved. The term therefore includes the various forms of colitis, pseudomembranous colitis, diarrhoea and antibiotic-associated disease.

As used herein, the term "selective Clostridium difficile agent" is used herein to define a compound which exhibits bacteriostatic and/or bacteriocidal activity against one or more strains of C. difficile but which does not exhibit bacteriostatic and/or bacteriocidal activity against one or more representative(s) of the normal gut flora selected from: (a) Escherichia spp. (for example, Escherichia coli); (b) Bacteroides spp. (for example, B. fragilis); (c) Fusobacterium spp.; (d) Eubacterium spp. (e) Ruminococcus spp.; (f) Peptococcus spp.; (g) Peptostreptococcus spp.; (h) Bifidobacterium spp.; (i) Lactobacillus spp.; (j) Enterococcus spp. (for example, E. faecium); (k) clostridial species other than C. difficile (for example C. perfringens); (l) Enterobacter spp.; (m) Serratia app.; (n) Klebsiella app.; (o) Proteus spp.; (p) Pseudomonas spp. and (q) Veillonelta spp.

Preferred selective Clostridium difficile agents exhibit bacteriostatic and/or bacteriocidal activity against one or more strains of C. difficile but do not exhibit bacteriostatic and/or bacteriocidal activity against: (a) Escherichia coli or (b) B. fragilis.

Thus, certain preferred selective Clostridium difficile agents of the invention exhibit bacteriostatic and/or bacteriocidal activity against one or more strains of C. difficile but do not exhibit bacteriostatic and/or bacteriocidal activity against B. fragilis.

As used herein, the term "bacterial infection" is used to define a condition in which a subject is infected with a bacterium. The infection may be symptomatic or asymptomatic. In the latter case, the subject may be identified as infected on the basis of various tests, including for example biochemical tests, serological tests, microbiological culture and/or microscopy.

The terms bacteriostatic and bacteriocidal are terms of art used to define the ability to prevent (or reduce the rate of) bacterial growth and to mediate (directly or indirectly) the cellular destruction of bacterial cells, respectively. The terms are not mutually exclusive, and many agents exert both bacteriostatic and bacteriocidal effects (in some cases in a dose-specific or target-specific manner). In general, bacteriocidal agents yield better therapeutic results and are preferred.

As used herein, the term "broad spectrum antibiotic" defines an agent which is bacteriocidal and/or bacteriostatic for a range of bacteria including both Gram-positive and Gram-negative bacteria.

The "term multi-drug resistant" (MDR) as applied herein to a bacterium defines a bacterium which is resistant to two or more classes of antibiotics including, but not limited to, antibiotics selected from penicillin, methicillin, quinolone, macrolide and/or vancomycin.

As used herein, the term "treatment" or "treating" refers to an intervention (e.g. the administration of an agent to a subject) which cures, ameliorates or lessens the symptoms of a disease or removes (or lessens the impact of) its cause(s) (for example, the causative bacterium). In this case, the term is used synonymously with the term "therapy". Thus, the treatment of infection according to the invention may be characterized by the (direct or indirect) bacteriostatic and/or bacteriocidal action of the compounds of the invention.

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

The term "subject" (which is to be read to include "individual", "animal", "patient" or "mammal" where context permits) defines any subject, particularly a mammalian subject, for whom treatment is indicated. Mammalian subjects include, but are not limited to, humans, primates, domestic animals, farm animals, pet animals and rodents such as mice, rats, hamsters and guinea pigs. In preferred embodiments, the subject is a human.

The term Gram-positive bacterium is a term of art defining a particular class of bacteria that are grouped together on the basis of certain cell wall staining characteristics.

The term low G+C Gram-positive bacterium is a term of art defining a particular subclass class of evolutionarily related bacteria within the Gram-positives on the basis of the composition of the bases in the DNA. The subclass includes *Streptococcus* spp., *Staphylococcus* spp., *Listeria* spp., *Bacillus* spp., *Clostridium* spp., *Enterococcus* spp. and *Lactobacillus* spp.

The term "minimum inhibitory concentration" or 'MIC' defines the lowest concentration of a test compound that is needed to inhibit growth of a bacterial isolate in vitro. A common method for determining the MIC of an antibiotic is to prepare several tubes containing serial dilutions of the test compound that are then inoculated with the bacterial isolate of interest. Following incubation at appropriate atmosphere and temperature, the MIC of an antibiotic can be determined from the tube with the lowest concentration that shows no turbidity.

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:
  compositions (e.g. unitary formulations) comprising the two or more compounds/agents in admixture (for example within the same unit dose);
  compositions comprising material in which the two or more compounds/agents are chemically/physicochemically linked (for example by crosslinking, molecular agglomeration or binding to a common vehicle moiety);
  compositions comprising material in which the two or more compounds/agents are chemically/physicochemically co-packaged (for example, disposed on or within lipid vesicles, particles (e.g. micro- or nanoparticles) or emulsion droplets);
  pharmaceutical kits, pharmaceutical packs or patient packs in which the two or more compounds/agents are co-packaged or co-presented (e.g. as part of an array of unit doses);
Examples of non-physically associated combined compounds/agents include:
  material (e.g. a non-unitary formulation) comprising at least one of the two or more compounds/agents together with instructions for the extemporaneous association of the at least one compound/agent to form a physical association of the two or more compounds/agents;
  material (e.g. a non-unitary formulation) comprising at least one of the two or more compounds/agents together with instructions for combination therapy with the two or more compounds/agents;
  material comprising at least one of the two or more compounds/agents together with instructions for administration to a patient population in which the other(s) of the two or more compounds/agents have been (or are being) administered;
  material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The combinations of the invention may produce a therapeutically efficacious effect relative to the therapeutic effect of the individual compounds/agents when administered separately.

As used herein, an effective amount or a therapeutically effective amount of a compound defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The term "efficacious" includes advantageous effects such as additivity, synergism, reduced side effects, reduced toxicity or improved performance or activity. Advantageously, an efficacious effect may allow for lower doses of each or either component to be administered to a patient, thereby decreasing the toxicity, whilst producing and/or maintaining the same therapeutic effect. A synergistic effect in the present context refers to a therapeutic effect produced by the combination which is larger than the sum of the therapeutic effects of the components of the combination when presented individually. An additive effect in the present context refers to a therapeutic effect produced by the combination which is larger than the therapeutic effect of any of the components of the combination when presented individually.

The term "ancillary compound" (or "ancillary agent") as used herein is intended to define any compound which yields an efficacious combination (as herein defined) when combined with a compound of the invention. The ancillary compound may therefore act as an adjunct to the compound of the invention, or may otherwise contribute to the efficacy of the combination (for example, by producing a synergistic or additive effect or by potentiating the activity of the compound of the invention).

The term "adjunctive" as applied to the use of the compounds and combinations of the invention in therapy or prophylaxis defines uses in which the materials are administered together with one or more other drugs, interventions, regimens or treatments (such as surgery and/or irradiation). Such adjunctive therapies may comprise the concurrent, separate or sequential administration/application of the materials of the invention and the other treatment(s). Thus, in some embodiments, adjunctive use of the materials of the invention is reflected in the formulation of the pharmaceutical compositions of the invention. For example, adjunctive use may be reflected in a specific unit dosage, or in formulations in which the compound of the invention is present in admixture with the other drug(s) with which it is to be used adjunctively (or else physically associated with the other drug(s) within a single unit dose). In other embodiments, adjunctive use of the compounds or compositions of the invention may be reflected in the composition of the pharmaceutical kits of the invention, wherein the compound of the invention is co-packaged (e.g. as part of an array of unit doses) with the other drug(s) with which it is to be used adjunctively. In yet other embodiments, adjunctive use of the compounds of the invention may be reflected in the content of the information and/or instructions co-packaged with the compound relating to formulation and/or posology.

The term pharmaceutically acceptable derivative as applied to the compounds of the invention define compounds which are obtained (or obtainable) by chemical derivatization of the parent compounds of the invention. The pharmaceutically acceptable derivatives are therefore suitable for administration to or use in contact with mammalian tissues without undue toxicity, irritation or allergic response (i.e. commensurate with a reasonable benefit/risk ratio). Preferred derivatives are those obtained (or obtainable) by alkylation, esterification or acylation of the parent compounds of the invention. The derivatives may be active per se, or may be inactive until processed in vivo. In the latter case, the derivatives of the invention act as prodrugs. Particularly preferred prodrugs are ester derivatives which are esterified at one or more of the free hydroxyls and which are activated by hydrolysis in vivo. Other preferred prodrugs are covalently bonded compounds which release the active parent drug according to general formula (I) after cleavage of the covalent bond(s) in vivo.

The pharmaceutically acceptable derivatives of the invention retain some or all of the activity of the parent compound. In some cases, the activity is increased by derivatization. Derivatization may also augment other biological activities of the compound, for example bioavailability.

The term pharmaceutically acceptable salt as applied to the compounds of the invention defines any non-toxic organic or inorganic acid addition salt of the free base compound which is suitable for use in contact with mammalian tissues without undue toxicity, irritation, allergic response and which are commensurate with a reasonable benefit/risk ratio. Suitable pharmaceutically acceptable salts are well known in the art. Examples are the salts with inorganic acids (for example hydrochloric, hydrobromic, sulphuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid). The compounds of the invention may also be converted into salts by reaction with an alkali metal halide, for example sodium chloride, sodium iodide or lithium iodide. Preferably, the compounds of the invention are converted into their salts by reaction with a stoichiometric amount of sodium chloride in the presence of a solvent such as acetone.

These salts and the free base compounds can exist in either a hydrated or a substantially anhydrous form. Crystalline forms of the compounds of the invention are also contemplated and in general the acid addition salts of the compounds of the invention are crystalline materials which are soluble in water and various hydrophilic organic solvents and which in comparison to their free base forms, demonstrate higher melting points and an increased solubility.

The term pharmaceutically acceptable solvate as applied to the compounds of the invention defines any pharmaceutically acceptable solvate form of a specified compound that retains the biological effectiveness of such compound. Examples of solvates include compounds of the invention in combination with water (hydrates), isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulae include compounds having the indicated structure, including the hydrated as well as the non-hydrated forms.

The term pharmaceutically acceptable prodrug as applied to the compounds of the invention defines any pharmaceutically acceptable compound that may be converted under physiological conditions or by solvolysis to the specified compound, to a pharmaceutically acceptable salt of such compound or to a compound that shares at least some of the antibacterial activity of the specified compound (e.g. exhibiting activity against Clostridium difficile).

The term pharmaceutically acceptable metabolite as applied to the compounds of the invention defines a pharmacologically active product produced through metabolism in the body of the specified compound or salt thereof.

Prodrugs and active metabolites of the compounds of the invention may be identified using routine techniques known in the art (see for example, Bertolini et al., J. Med. Chem., 1997, 40, 2011-2016).

The term pharmaceutically acceptable complex as applied to the compounds of the invention defines compounds or compositions in which the compound of the invention forms a component part. Thus, the complexes of the invention include derivatives in which the compound of the invention is physically associated (e.g. by covalent or non-covalent bonding) to another moiety or moieties. The term therefore includes multimeric forms of the compounds of the invention. Such multimers may be generated by linking or placing multiple copies of a compound of the invention in close proximity to each other (e.g. via a scaffolding or carrier moiety).

The term bioisostere (or simply isostere) is a term of art used to define drug analogues in which one or more atoms (or groups of atoms) have been substituted with replacement atoms (or groups of atoms) having similar steric and/or electronic features to those atoms which they replace. The substitution of a hydrogen atom or a hydroxyl group with a fluorine atom is a commonly employed bioisosteric replacement. Sila-substitution (C/Si-exchange) is a relatively recent technique for producing isosteres. This approach involves the replacement of one or more specific carbon atoms in a compound with silicon (for a review, see Tacke and Zilch (1986) Endeavour, New Series 10: 191-197). The sila-substituted isosteres (silicon isosteres) may exhibit improved pharmacological properties, and may for example be better tolerated, have a longer half-life or exhibit increased potency (see for example Englebienne (2005) Med. Chem., 1(3): 215-226). Similarly, replacement of an atom by one of its isotopes, for example hydrogen by deuterium, may also lead to improved pharmacological properties, for example leading to longer half-life (see for example Kushner et al (1999) Can J Physiol Pharmacol. 77(2):79-88). In its broadest aspect, the present invention contemplates all bioisosteres (and specifically, all silicon bioisosteres) of the compounds of the invention.

In its broadest aspect, the present invention contemplates all optical isomers, racemic forms and diastereoisomers of the compounds described herein. Those skilled in the art will appreciate that, owing to the asymmetrically substituted carbon atoms present in the compounds of the invention, the compounds may be produced in optically active and racemic forms. If a chiral centre or another form of isomeric centre is present in a compound of the present invention, all forms of such isomer or isomers, including enantiomers and diastereoisomers, are intended to be covered herein. Compounds of the invention containing a chiral centre (or multiple chiral centres) may be used as a racemic mixture, an enantiomerically enriched mixture, or the racemic mixture may be separated using well-known techniques and an individual enantiomer may be used alone. Thus, references to the compounds of the present invention encompass the products as a mixture of diastereoisomers, as individual diastereoisomers, as a mixture of enantiomers as well as in the form of individual enantiomers.

Therefore, the present invention contemplates all optical isomers and racemic forms thereof of the compounds of the invention, and unless indicated otherwise (e.g. by use of dash-wedge structural formulae) the compounds shown herein are intended to encompass all possible optical isomers of the compounds so depicted. In cases where the stereochemical form of the compound is important for pharmaceutical utility, the invention contemplates use of an isolated eutomer.

In the present specification the term "alkyl" defines a straight or branched saturated hydrocarbon chain. The term "$C_1$-$C_6$ alkyl" refers to a straight or branched saturated hydrocarbon chain having one to six carbon atoms. Examples include methyl, ethyl, n-propyl, isopropyl, t-butyl, n-hexyl. The term "$C_1$-$C_9$ alkyl" refers to a straight or branched saturated hydrocarbon chain having one to nine carbon atoms. The term "$C_1$-$C_{15}$ alkyl" refers to a straight or branched saturated hydrocarbon chain having one to fifteen carbon atoms. The alkyl groups of the invention may be optionally substituted by one or more halogen atoms.

"$C_1$-$C_4$ alkyl" has a similar meaning except that it contains from one to four carbon atoms.

"$C_2$-$C_6$ alkenyl" refers to a straight or branched hydrocarbon chain having from two to six carbon atoms and containing at least one carbon-carbon double bond. Examples include ethenyl, 2-propenyl, and 3-hexenyl.

The term "$C_1$-$C_6$ haloalkyl" refers to a $C_{1-6}$ alkyl group as defined above substituted by one or more halogen atoms.

In the present specification the term "alkenyl" defines a straight or branched hydrocarbon chain having containing at least one carbon-carbon double bond. The term "$C_1$-$C_6$ alkenyl" refers to a straight or branched unsaturated hydrocarbon chain having one to six carbon atoms. The term "$C_1$-$C_9$ alkenyl" refers to a straight or branched unsaturated hydrocarbon chain having one to nine carbon atoms. The term "$C_1$-$C_{15}$ alkenyl" refers to a straight or branched unsaturated hydrocarbon chain having one to fifteen carbon atoms. Preferred is $C_1$-$C_6$ alkenyl. Examples include ethenyl, 2-propenyl, and 3-hexenyl. The alkenyl groups of the invention may be optionally substituted by one or more halogen atoms.

In the present specification the term "alkynyl" defines a straight or branched hydrocarbon chain having containing at least one carbon-carbon triple bond. The term "$C_1$-$C_6$ alkynyl" refers to a straight or branched unsaturated hydrocarbon chain having one to six carbon atoms. The term "$C_1$-$C_9$ alkynyl" refers to a straight or branched unsaturated hydrocarbon chain having one to nine carbon atoms. The term "$C_1$-$C_{15}$ alkynyl" refers to a straight or branched unsaturated hydrocarbon chain having one to fifteen carbon atoms. Preferred is $C_1$-$C_6$ alkynyl. Examples include ethynyl, 2-propynyl, and 3-hexynyl. The alkynyl groups of the invention may be optionally substituted by one or more halogen atoms.

The term "heterocyclyl" defines a saturated or partially saturated 3 to 14 membered ring system (except when alternative numbers of ring atoms are specified) similar to cycloalkyl but in which at least one of the carbon atoms has been replaced by N, O, S, SO or $SO_2$. Examples include piperidine, piperazine, morpholine, tetrahydrofuran and pyrrolidine.

As used herein, the term "carbocyclyl" means a mono- or polycyclic residue containing 3 or more (e.g. 3-14, 3-10 or 3-8) carbon atoms. The carbocyclyl residues of the invention may be optionally substituted by one or more halogen atoms. Mono- and bicyclic carbocyclyl residues are preferred. The carbocyclyl residues can be saturated or partially unsaturated and include fused bicyclic or tricyclic systems. Examples of such groups include cyclopropyl, cyclobutyl, cyclopentyl, cyclohexyl, cyclohexenyl and also bridged systems such as norbornyl and adamantyl.

Saturated carbocyclyl residues are preferred and are referred to herein as "cycloalkyls" and the term "cycloalkyl" is used herein to define a saturated 3 to 14 membered carbocyclic ring including fused bicyclic or tricyclic systems. Examples of such groups include cyclopropyl, cyclobutyl, cyclopentyl, cyclohexyl and also bridged systems such as norbornyl and adamantyl. The cycloalkyl residues of the invention may be optionally substituted by one or more halogen atoms.

In the present specification the term "aryl" defines a 5-14 (e.g. 5-10) membered aromatic mono-, bi- or tricyclic group at least one ring of which is aromatic. Thus, bicyclic aryl groups may contain only one aromatic ring. Examples of aromatic moieties are benzene, naphthalene, imidazole and pyridine. The term also includes bicyclic or tricyclic systems in which one or more of the rings has aromatic character. Indane is an example of this type of system.

As used herein, the term "heteroaryl" are aryl moieties as defined above which contain heteroatoms (e.g. nitrogen, sulphur and/or oxygen). The term also includes systems in which a ring having aromatic character is fused to a saturated or partially saturated ring. Examples include pyridine, pyrimidine, furan, thiophene, indole, isoindole, indoline, benzofuran, benzimidazole, benzimidazoline quinoline, isoquinoline, tetrahydroisoquinoline, quinazoline, thiazole, benzthiazole, benzoxazole, indazole and imidazole ring systems. Unless otherwise indicated, the term "aryl" is to be interpreted to include heteroaryl groups as defined above.

The aryl and heteroaryl groups of he invention may optionally substituted by one or more halogen atoms.

In the present specification, "halo" refers to fluoro, chloro, bromo or iodo.

In the general formulae of the present invention (and in particular in general formula (I) as described below), the bond orders of the specified rings may vary when the various possible heteroatom(s) imply specific requirements in order to satisfy aromaticity, prevent antiaromaticity and stabilize tautomeric forms due to localization. In such cases, the appropriate bond orders of the ring structures in the structural formulae of the present invention are contemplated herein.

The term "symmetrical" as applied to the compounds formula (I) may define compounds in which the substituents $R^1$ and $R^2$ are the same.

The term "unsymmetrical" applied to the compounds of formula (I) may define compounds in which the substituents $R^1$ and $R^2$ are different.

(2) Compounds According to the Invention (2) Structure Considerations

Particularly preferred compounds of en formula (I) are listed in Table 1 (below:

TABLE 1

| Compound number | Compound Name |
|---|---|
| 1 | 2-(2'-(pyridin-4-yl)-1H,1'H-5,5'-bibenzo[d]imidazol-2-yl)thieno[2,3-b]pyridine |
| 2 | 2-(benzo[b]thiophen-2-yl)-2'-(pyridin-4-yl)-1H,1'H-5,5'-bibenzo[d]imidazole |
| 3 | 2-(benzofuran-5-yl)-2'-(pyridin-4-yl)-1H,1'H-5,5'-bibenzo[d]imidazole |
| 4 | 6-(2'-(pyridin-4-yl)-1H,3'H-5,5'-bibenzo[d]imidazol-2-yl)benzo[d]imidazole |
| 5 | 2-(benzo[b]thiophen-5-yl)-2'-(pyridin-4-yl)-1H,3'H-5,5'-bibenzo[d]imidazole |
| 6 | 2-(1H-indol-5-yl)-2'-(pyridin-4-yl)-1H,3'H-5,5'-bibenzo[d]imidazole |
| 7 | 2-(2,3-dihydrobenzofuran-5-yl)-2'-(pyridin-4-yl)-1H,3'H-5,5'-bibenzo[d]imidazole |
| 8 | 2-(imidazo[1,2-a]pyridin-6-yl)-2'-(pyridin-4-yl)-1H,1'H-5,5'-bibenzo[d]imidazole |
| 9 | 2-(benzo[d][1,3]dioxol-5-yl)-2'-(pyridin-4-yl)-1H,1'H-5,5'-bibenzo[d]imidazole |
| 10 | 2-(benzofuran-2-yl)-2'-(pyridin-4-yl)-1H,1'H-5,5'-bibenzo[d]imidazole |
| 11 | 2-(2'-(pyridin-4-yl)-1H,1'H-[5,5'-bibenzo[d]imidazol]-2-yl)thieno[2,3-c]pyridine |
| 12 | 2-(imidazo[1,2-a]pyridin-6-yl)-2'-(pyridin-3-yl)-1H,1'H-5,5'-bibenzo[d]imidazole |
| 13 | 2-(2'-(pyridin-3-yl)-1H,1'H-[5,5'-bibenzo[d]imidazol]-2-yl)thieno[2,3-b]pyridine |

In each case, the invention contemplates pharmaceutically acceptable salts, hydrates, solvates, complexes, bioisosteres, metabolites or prodrugs of each of the listed compounds.

References o particular compound numbers herein refer to the numbers in Table 1.

Certain of the compounds of general formula (I) are novel. Thus, according to the invention, the invention contemplates those compounds of general formula (I) which are novel as compounds per se, together with processes for their preparation, compositions containing them, as well as their use as pharmaceuticals.

Thus, the invention contemplates a compound selected from:
2-(2'-(pyridin-4-yl)-1H,1'H-5,5'-bibenzo[d]imidazol-2-yl)thieno[2,3-b]pyridine
2-(benzo[b]thiophen-2-yl)-2'-(pyridin-4-yl)-1H,1'H-5,5'-bibenzo[d]imidazole
2-(benzofuran-5-yl)-2'-(pyridin-4-yl)-1H,1'H-5,5'-bibenzo[d]imidazole
6-(2'-(pyridin-4-yl)-1H,3'H-5,5'-bibenzo[d]imidazol-2-yl)benzo[d]imidazole
2-(benzo[b]thiophen-5-yl)-2'-(pyridin-4-yl)-1H,3'H-5,5'-bibenzo[d]imidazole
2-(1H-indol-5-yl)-2'-(pyridin-4-yl)-1H,3'H,5,5'-bibenzo[d]imidazole
2-(2,3-dihydrobenzofuran-5-yl)-2'-(pyridin-4-yl)-1H,3'H-5,5'-bibenzo[d]imidazole
2-(imidazo[1,2-a]pyridin-6-yl)-2'-(pyridin-4-yl)-1H,1'H-5,5'-bibenzo[d]imidazole
2-(benzo[d][1,3]dioxol-5-yl)-2'-(pyridin-4-yl)-1H,1'H-5,5'-bibenzo[d]imidazole
2-(benzofuran-2-yl)-2'-(pyridin-4-yl)-1H,1'H-5,5'-bibenzo[d]imidazole
2-(2'-(pyridin-4-yl)-1H,1'H-[5,5'-bibenzo[d]imidazol]-2-yl)thieno[2,3-c]pyridine
2-(imidazo[1,2-a]pyridin-6-yl)-2'-(pyridin-3-yl)-1H,1'H-5,5'-bibenzo[d]imidazole
2-(2'-(pyridin-3-yl)-1H,1'H-[5,5'-bibenzo[d]imidazol]-2-yl)thieno[2,3-b]pyridine or a pharmaceutically acceptable N-oxide, salt, hydrate, solvate, complex, bioisostere, metabolite or prodrug thereof, as well as compositions (for example pharmaceutical compositions) comprising said compounds.

(b) Functional Considerations (i) Effect and Selectivity Against Strains of *Clostridium difficile*

Preferred compounds of the invention may be selective *Clostridium difficile* agents, as hereinbefore defined.

Particularly preferred selective *Clostridium difficile* agents exhibit bacteriostatic and/or bacteriocidal activity against one or more strains of *C. difficile* but do not exhibit bacteriostatic and/or bacteriocidal activity (MIC>64 µg/mL) against *B. fragilis* ATCC25285.

Yet more particularly preferred selective *Clostridium difficile* agents exhibit bacteriostatic and/or bacteriocidal activity against one or more strains of *C. difficile* but do not exhibit bacteriostatic and/or bacteriocidal activity (MIC>64 µg/mL) against both *Bacteroides fragilis* ATCC25285 and *Escherichia coli* ATCC25922.

The preferred compounds of the invention which are selective *Clostridium difficile* agents can therefore be used to treat MAD without disturbing the existing gut flora to a clinically significant extent. Thus, such compounds may be used as antimicrobial agents without causing antibiotic-associated disease (as defined herein) and/or the spread of antibiotic resistant strains of gut pathogens.

Compounds of the invention which act as selective *Clostridium difficile* agents may be identified by determining the relative antibacterial activities of the compound for *Clostridium difficile* and one or more indicator organism(s) representative of the normal gut flora. Suitable indicator organisms for this purpose include: (a) *Escherichia* spp. (for example, *Escherichia coli*); (b) *Bacteroides* spp. (for example, *B. fragilis*); (c) *Fusobacterium* spp.; (d) *Eubacterium* spp. (e) *Ruminococcus* spp.; (f) *Peptococcus* spp.; (g) *Peptostreptococcus* asp.; (h) *Bifidobacterium* spp.; (i) *Lactobacillus* spp.; (j) *Enterococcus* spp. (for example, *E. faecium*); (k) clostridial species other than *C. difficile* (for example *C. perfringens*); (l) *Enterobacter* spp.; (m) *Serratia* spp.; (n) *Klebsiella* app.; (o) *Proteus* spp.; (p) *Pseudomonas* spp. and (q) *Veillonella* spp.

Alternatively, or in addition, compounds of the invention which act as selective *Clostridium difficile* agents may be identified by performing quantitative stool cultures on serial stool samples obtained from subjects dosed with the a test compound. An in vitro variant of this approach is based on determining whether the test compound produces major floral shifts when incubated with diluted and filtered faecal samples in vitro. In this case, floral shifts may be detected by determining the effect of the test compound on the relative numbers of bacteria representative of two or more of the following genera: (a) *Escherichia* spp. (for example, *Escherichia coli*); (b) *Bacteroides* spp. (for example, *B. fragilis*); (c) *Fusobacterium* spp.; (d) *Eubacterium* spp. (e) *Ruminococcus* spp.; (f) *Peptococcus* spp.; (g) *Peptostreptococcus* spp.; (h) *Bifidobacterium* spp.; (i) *Lactobacillus* spp.; (j) *Enterococcus* spp. (for example, *E. faecium*); (k) clostridial species other than *C. difficile* (for example *C. perfringens*); (l) *Enterobacter* spp.; (m) *Serratia* spp.; (n) *Klebsiella* spp.; (o) *Proteus* spp.; (p) *Pseudomonas* spp. and (q) *Veillonella* spp.

Thus, h invention contemplates a selective *Clostridium difficile* agent selected from:

2-(2'-(pyridin-4-yl)-1H,1'H-5,5'-bibenzo[d]imidazol-2-yl)thieno[2,3-b]pyridine 2-(benzo[b]thiophen-2-yl)-2'-(pyridin-4-yl)-1H,1'H-5,5'-bibenzo[d]imidazole 2-(benzofuran-5-yl)-2'-(pyridin-4-yl)-1H,1'H-5,5'-bibenzo[d]imidazole 6-(2'-(pyridin-4-yl)-1H,3'H-5,5'-bibenzo[d]imidazol-2-yl)benzo[d]imidazole 2-(benzo[b]thiophen-5-yl)-2'-(pyridin-4-yl)-1H,3'H-5,5'-bibenzo[d]imidazole 2-(1H-indol-5-yl)-2'-(pyridin-4-yl)-1H,3'H-5,5'-bibenzo[d]imidazole 2-(2,3-dihydrobenzofuran-5-yl)-2'-(pyridin-4-yl)-1H,3'H-5,5'-bibenzo[d]imidazole 2-(imidazo[1,2-a]pyridin-6-yl)-2'-(pyridin-4-yl)-1H,1'H-5,5*-bibenzo[d]imidazole 2-(benzo[d][1,3]dioxol-5-yl)-2'-(pyridin-4-yl)-1H,1'H-5,5'-bibenzo[d]imidazole 2-(benzofuran-2-yl)-2'-(pyridin-4-yl)-1H,1'H-5,5'-bibenzo[d]imidazole 2-(2'-(pyridin-4-yl)-1H,1'H-[5,5'-bibenzo[d]imidazol]-2-yl)thieno[2,3-b]pyridine 2-(imidazo[1,2-a]pyridin-6-yl)-2'-(pyridin-3-yl)-1H,1'H-5,5-bibenzo[d]imidazole 2-(2'-(pyridin-3-yl)-1H,1'H-[5,5'-bibenzo[d]imidazol]-2-yl)thieno[2,3-b]pyridine or a pharmaceutically acceptable N-oxide, salt, hydrate, solvate, complex, bioisostere, metabolite or prodrug thereof.

(ii) Effect on Spore Germination

The compounds of the invention may inhibit or prevent spore germination.

Compounds which inhibit spore germination can be identified by in vitro detection of alterations in endospore refractivity, heat resistance and staining: germinating endospores become phase dark, susceptible to heat and stainable with certain dyes.

(iii) Effect on Spore Outgrowth

The compounds of he invention may inhibit or prevent spore outgrowth.

Compounds which inhibit spore outgrowth can be identified by microscopic examination of spores exposed to germinants in vitro.

(iv) Bacteriocidal and/or Bacteriostatic Effect

The compounds of he invention may be bacteriocidal and/or bacteriostatic.

Preferred are bacteriocidal compounds as hereinbefore defined. Such bacteriocidal compounds may also be bacteriostatic (e.g. depending on target bacterium and concentration).

III. Medical Applications (a) Treatment of *C. difficile* Infection

The compounds of the invention find application in the treatment of *Clostridium difficile* infection or disease.

Particularly preferred is the treatment of *Clostridium difficile*-associated disease (CDAD) defines a set of symptoms and diseases associated with *C. difficile* infection and/or intoxication. CDAD includes diarrhoea, bloating, flu-like symptoms, fever, appetite loss, abdominal pain, nausea, dehydration and bowel inflammation (colitis). The most serious manifestation of CDAD is pseudomembraneous colitis (PMC), which is manifested histologically by colitis with mucosal plaques, and clinically by severe diarrhoea, abdominal cramps and systemic toxicity.

The compounds of the invention find application in the treatment of all forms of CDAD, including diarrhoea, bloating, flu-like symptoms, fever, appetite loss, abdominal pain, nausea, dehydration, colitis and pseudomembraneous colitis.

The invention also finds application in the treatment of intoxication with clostridial exotoxins, including *Clostridium difficile* toxin A (TcdA), toxin B (TcdB) and/or binary toxin CDT. Thus, the compounds of the invention find application in the treatment of a disease caused (or exacerbated) by the presence of *Clostridium difficile* toxins A (TcdA), B (TcdB) and/or binary toxin CDT.

(b) Treatment of Antibiotic-Associated Disease

Antibiotic-associated disease defines conditions arising from changes in the relative amounts of the microorganisms constituting the normal gut flora caused by (partial) elimination of the flora by antibiotic administration. Such diseases arise when the administration of antibiotics (particularly broad-spectrum antibiotics) permits the growth of pathogenic organisms (either by overgrowth from endogenous populations usually kept in check by the normal gut flora or by opportunistic colonization of sites cleared of the normal gut flora by the antibiotic).

Antibiotic-associated diseases is typically manifested by diarrhoea (and associated dehydration), abdominal cramps, tenesmus and fever. It may also lead to various forms of colitis, including pseudomembraneous colitis (PMC). Thus, antibiotic-associated disease includes antibiotic-associated diarrhoea (AAD) and antibiotic-associated colitis (AAC).

Antibiotic-associated disease is often caused by toxin-producing strains of *Clostridium difficile, Staphylococcus aureus* (including methicillin-resistant *S. aureus*) and *Clostridium perfringens*. *Clostridium difficile* is the most common cause of nosocomial AAD and causes the majority of cases of AAMC. The bacterium proliferates in the colon of patients who have been given broad-spectrum antibiotics or cancer chemotherapy.

The compounds of the invention therefore find application in the treatment of antibiotic-associated disease, including AAD and AAC. Particularly preferred for use in such applications are compounds of the invention which are selective (as hereinbefore defined), since such compounds substantially spare the normal gut flora.

The compounds of the invention find particular application in the prophylaxis of antibiotic-associated disease, including AAD and AAC. In such applications, the compounds of the invention may be co-administered with other antibiotics or treatments which can induce changes in the relative amounts of the microorganisms constituting the normal gut flora.

Thus, the compounds of the invention may be used to treat subjects treated (or undergoing treatment) with broad-spectrum antibiotics.

(c) Treatment of Colitis, Pseudomembraneous Colitis and Diarrhoea

As explained above, bacteria selected from *Clostridium difficile, Staphylococcus aureus* and *Clostridium perfringens* are implicated in colitis, pseudomembraneous colitis (PMC) and diarrhoea.

Accordingly, the compounds of the invention find application in the treatment of colitis, pseudomembraneous colitis (PMC) or diarrhoea.

Particularly preferred is the treatment of pseudomembraneous colitis.

IV. Adjunctive Agents for Use in the Combinations of the Invention (a) General

In addition to the compound of the invention, the invention also contemplates the use of one or more of the following adjunctive agents as further components of the invention.

Thus, the invention provides compositions comprising the compound of the invention in combination with one or more adjunctive agents selected from those described below.

(b) Antiviral Adjunctive Agents

The combinations preferably further comprise one or more auxiliary antiviral agent(s). Such auxiliary antiviral agents may be selected from one or more of (a) viral enzyme inhibitors (for example selected from (i) protease inhibitors, (ii) helicase inhibitors and (iii) polymerase inhibitors); (b) nucleoside/nucleotide reverse transcriptase inhibitors; (c) non-nucleoside reverse transcriptase inhibitors; (d) integrase inhibitors; (e) maturation inhibitors; (f) cytokines or cytokine stimulatory factors; (g) viral entry inhibitors, for example selected from: (i) an attachment inhibitor; (ii) a co-receptor binding inhibitor; and (iii) a membrane fusion inhibitor.

(c) Antibacterial Adjunctive Agents

The compounds of the invention may be used in combination with various antibacterial agents, including, but not limited to one or more antibiotic(s) selected from the following:

Aminoglycosides (for example amikacin, gentamicin, kanamycin, neomycin, netilmicin, streptomycin, tobramycin and paromomycin).

Ansamycins (for example geldanarnycin and herbimycin)

Carbacephems (for example loracarbef).

Carbapenems (for example ertapenem, doripenem, imipenem/cilastatin and meropenem)

Cephalosporins (first generation), including for example cefadroxil, cefazolin, cefalotin/cefalothin and cephalexin).

Cephalosporins (second generation), including for example cefaclor, cefamandole, cefoxitin, cefprozil and cefuroxime.

Cephalosporins (third generation), including for example cefixime, cefdinir, cefditoren, cefoperazone, cefotaxime, cefpodoxime, ceftazidime, ceftibuten, ceftizoxime, ceftriaxone and cefdinir.

Cephalosporins (fourth generation), including for example cefepime.

Glycopeptides (for example vancomycin and teicoplanin).

Macrolides (for example azithromycin, clarithromycin, dirithromycin, erythromycin, roxithromycin, troleandomycin, telithromycin and spectinomycin).

Monobactams (for example aztreonam).

Penicillins (for example amoxicillin, ampicillin, azlocillin, carbenicillin, cloxacillin, dicloxacillin, flucloxacillin, mezlocillin, nafcillin, penicillin, piperacillin and ticarcillin), Polypeptides (for example bacitracin, polymixin B and colistin).

Quinolones (for example ciprofloxacin, enoxacin, gatifloxacin, levofloxacin, lomefloxacin, moxifloxacin, norfloxacin, ofloxacin and trovafloxacin).

Sulfonamides (for example mafenide, prontosil, sulfacetamide, sulfa ethizole, sulfanilimide, sulfasalazine, sulfisoxazole, trimethoprim, trimethoprim-sulfamethoxazole (co-trimoxazole, TMP-SMX)).

Tetracyclines (for example demeclocycline, doxycycline, minocycline, oxytetracycline and tetracycline).

Aminocoumarins (for example novobiocin, albamycin, coumermycin and clorobiocin).

Oxazolidinones (for example linezolid and AZD2563).

Lipopeptides (for example daptomycin).

Streptogramins (for example quinupristin/dalfopristin),

Glycylcyclines (for example tigecycline).

Lantibiotics (for example Type A Lantibiotics (such as nisin, subtilin, epidermin, mutacin II, mutacin I & III) and Type B Lantibiotics (such as mersacidin, actagardine and cinnamycin).

Other suitable antibiotics useful as adjunctive agents include one or more antibiotic(s) selected from the following:

arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin and tinidazole.

Thus, the compounds of the invention may be used in combination with one or more antibiotics selected from: penicillin, cloxacillin, dicloxacillin, methicillin, nafcillin, oxacillin, ampicillin, amoxicillin, bacampicillin, capreomycin, cycloserine, azlocillin, carbenicillin, mezlocillin, piperacillin, ticarcillin, azithromycin, clarithromycin, clindamycin, erythromycin, lincomycin, demeclocycline, doxycycline, ethambutol, ethionamide, minocycline, oxytetracycline, tetracycline, quinolone, cinoxacin, nalidixic acid, fluoroquinolones (for example levofloxacin, moxafloxacin and gatifloxacin, ciprofloxacin, enoxacin, grepafloxacin), kanamycin, levofloxacin, lomefloxacin, norfloxacin, ofloxacin, p-aminosalicylic acid, sparfloxacin, trovafloxacin, bacitracin, colistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, streptomycin, nitrofurantoin, co-trimoxazole, rifamycin and derivatives thereof (for example rifampicin, rifabutin and rifapentine), isoniazid, pyrazinamide, kirromycin, thiostrepton, micrococcin, fusidic acid, thiolactomycin and fosmidomycin.

Other suitable antibacterial adjunctive agents may be selected from those listed in the table below:

| Compound | Class |
|---|---|
| DU-6859 | Fluoroquinolone |
| Erythromycin stinoprate | Macrolide |
| Oritavancin | Glycopeptide |
| Telavancin | Glycopeptide |
| Dalbavancin | Glycopeptide |
| Ceftobiprole medocaril | Cephalosporin |
| Tebipenem pivoxil | Carbapenem |
| Iclaprim | DHFR |
| OPT-80 | Difimicin |
| Ceftaroline fosamil | Cephalosporin |
| RX-3341 | Fluoroquinolone |
| Cethromycin | Ketolide |
| TD-1792 | Glycopeptide-β-lactam dimer |
| EDP-420 | Macrolide |
| RX-1741 | Oxazolidinone |
| MK-2764 | Glycycline |
| Nemonoxacin | Fluoroquinolone |
| Flopristin + Linopristin | Streptogramin |
| Tomopenem | Carbapenem |
| Ramoplanin | Glycolipodepsipeptide |
| Linezolid | Oxazolidinone |
| Cefditoren pivoxil | Cephalosporin |
| Ertapenem | Carbapenem |
| Gemifloxacin | Fluoroquinolone |
| Daptomycin | Lipopetide |
| Telithromycin | Lipopetide |
| Tigecyline | Glycylcycline |

(d) Antifungal Adjunctive Agents

The compounds of the invention may be used in combination with various antifungal agents (antimycotics).

(e) Antiprotozoal Adjunctive Agents

The compounds of the invention may be used in combination with various antiprotozoal agents, including but not limited to, chloroquine, doxycycline, mefloquine, metronidazole, eplornithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine and sulfadiazine.

(f) Other Adjunctive Agents

The compounds of the invention may be co-administered with a variety of other co-therapeutic agents which treat or prevent side effects arising from the antiinfective treatment and/or presenting as sequelae of the infection. Adjunctive agents of this type may or may not have antiinfective activity and include, for example, PPIs and H2RAs (as hereinbefore described).

Thus, the compounds of the invention may be used adjunctively with PPIs including, but are not limited to, omeprazole (Losec, Prilosec, Zegerid), lansoprazole (Prevacid, Zoton, Inhibitol), esomeprazole (Nexium), pantoprazole (Protonix, Somac, Pantoloc, Pantozol, Zurcal, Pan) and rabeprazole (Rabecid, Aciphex, Pariet, Rabeloc).

The compounds of the invention may also be used adjunctively with H2RAs including, but not limited to, cimetidine (Tagamet), ranitidine (Zinetac, Zantac), famotidine, (Pepcidine, Pepcid), roxatidine (Roxit) and nizatidine (Tazac, Axid).

The compounds of the invention may be used adjunctively with triple therapy with PPIs or H2RAs together with a combination of two antibiotics (including, but not limited to, antibiotics selected from metronidazole, amoxicillin, levofloxacin and clarithromycin).

Various probiotics may be used as adjunctive agents, including for example Saccharomyces boulardii or Lactobacillus acidophilus cells. Probiotics are mono or mixed cultures of live microorganisms which are proposed to help re-establish the natural gut microflora of the patient that has been disrupted by the offending antimicrobial that induced CDAD or even the agent used to treat CDAD. In addition, such microorganisms may act to stimulate the patient's immune system and to elicit production of enzymes that degrade the toxins associated with *C. difficile*. Particular microorganisms of interest are, but not limited to, *Saccharomyces* spp. (for example *Saccharomyces boulardli* and *Saccharomyces cerevisiae*) and *Lactobacillus* spp. (for example *Lactobacillus rhamnosus, Lactobacillus casei, Lactobaccillus acidophilus, Lactobacillus bulgaris* and *Lactobacillus plantarum*). Any other common probiotic composition or microorganism that is a normal member of the human intestinal tract may also be considered.

Pre-biotics, agents aimed at stimulating the growth of the intestinal flora, may also be used as adjunctive agents. For example, the use of oligofructose has been shown to increase levels of *Bifidobacterium* spp. and reduce subsequent relapse rates in patients. As such, any antibacterial agent with a narrow spectrum of activity targeted at *Clostridium* species would have significant benefit when dosed in combination with therapies aimed at reestablishing the normal enteric microorganism population.

Other approaches aimed at reestablishing the normal enteric flora include faecal biotherapy and faecal enemas prepared from the stools of healthy individuals which contain the normal microorganisms of the gut. Faecal bacteriotherapy may therefore also be used adjunctively with the compounds of the invention.

In order to sequester the toxins produced by *C. difficile*, absorbents which bind and sequester bacteriotoxins of various different types may be used as adjunctive agents. Ion exchange resins, such as the bile acid sequestrants cholsetyramine or colestipol, bind to the *C. difficile* cytotoxins and thus aim to reduce the degree of toxic challenge to the gut. However, ion exchange resins are known to bind to agents such as vancomycin and therefore may lead to suboptimal levels of antibacterial agent at the site of infection. Other absorbents that may be used adjunctively with the compounds of the invention include polymers such as Synsorb 90 and Tolevamer.

Although probiotic therapy is suggested to improve immune system response in CDAD patients, intravenous immunoglobulin (J. Antimicrob. Chem., 2004, 53, 882-884), for example, may also be used to treat CDAD patients, particularly recurrent cases where any further antimicrobial treatment would further exacerbate gut flora disturbance. Thus, the compounds of the invention may be used adjunctively with various immunoglobulins.

Although the use of agents aimed at reducing diarrhoea are generally avoided in CDAD patients, in certain cases it may be envisaged that the use of such agents in conjunction with an antibacterial may be of benefit when trying to increase levels of an antimicrobial agent at the site of infection and/or when trying to increase the length of time an antibacterial agent is in contact with the enteric pathogen. Such agents may include, but are not limited to, loperamide (Lopez, Imodium, Dimor, Pepto) diphenoxylate (Lomotil, Co-phenotrope) difenoxin (Motofen), and racecadotril. Thus, the compounds of the invention may be used adjunctively with various anti-diarrhoeal agents, including any of those listed above.

Co-therapeutic agents which treat or prevent any of the following side effects may be used as part of the same treatment regimen as the compounds of the invention: (a) lipodystrophy and wasting; (b) facial lipoatrophy; (c) hyperlipidemia; (d) fatigue; (e) anaemia; (f) peripheral neuropathy; (g) nausea; (h) diarrhoea; (i) hepatotoxicity; (j) osteopenia; (k) dehydration and (l) osteoporosis.

The treatment or prophylaxis may comprise the administration of a compound as defined herein as an adjunctive to one or more of the following treatments or interventions:
 (a) Cancer therapy;
 (b) AIDS therapy;
 (c) Immunosuppressive interventions;
 (d) Post-transplantation graft/implant management;
 (e) Onychomycotic nail surgery or debridement;
 (f) Topical antimycotic therapy (for example with an antimycotic agent selected from azoles, allylamines (e.g. terbinafine) or a morpholine (e.g. amorolfine);
 (g) Systemic antimycotic therapy;
 (h) Antibacterial therapy;
 (i) Antiviral therapy;
 (j) Anti-inflammation therapy (e.g. with steroids);
 (k) Analgesic administration;
 (l) Antipruritic administration;
 (m) Probiotic administration;
 (n) Faecal bacteriotherapy; or
 (o) Skin grafting.

Thus, the invention may comprise the treatment or prophylaxis of a patient population in which one or more of the treatment or interventions (a) to (o) are being (or have been) carried out.

(g) Adjunctive Treatments

The treatment or prophylaxis may comprise the administration of a compound as defined herein as an adjunctive to one or more of the following treatments or interventions:
 1. Cancer therapy;
 2. Immunosuppressive interventions;
 3. Immunostimulatory interventions;
 4. Post-transplantation graft/implant management;
 5. Onychomycotic nail surgery or debridement;
 6. Anti-inflammation therapy (e.g. with steroids);
 7. Analgesic administration;
 8. Antipruritic administration;
 9. Surgery;
 10. Cell or tissue ablation;
 11. Radiotherapy;
 12. Cryotherapy;
 13. Faecal transplantation therapy (faecal bacterio therapy);
 14. Probiotic therapy; or
 15. Skin grafting.

Thus, the invention may comprise the treatment or prophylaxis of a patient population in which one or more of the treatment or interventions (1) to (15) are being (or have been) carried out.

(V) Posology

The compounds of the present invention can be administered by oral or parenteral routes, including intravenous, intramuscular, intraperitoneal, subcutaneous, transdermal, airway (aerosol), rectal, vaginal and topical (including buccal and sublingual) administration.

The amount of the compound administered can vary widely according to the particular dosage unit employed, the period of treatment, the age and sex of the patient treated, the nature and extent of the disorder treated, and the particular compound selected.

In general, the effective amount of the compound administered will generally range from about 0.01 mg/kg to 10000 mg/kg daily. A unit dosage may contain from 0.05 to 500 mg of the compound, and can be taken one or more times per day. The compound can be administered with a pharmaceutical carrier using conventional dosage unit forms either orally, parenterally or topically, as described below.

The preferred route of administration is oral administration. In general a suitable dose will be in the range of 0.01 to 500 mg per kilogram body weight of the recipient per day, preferably in the range of 0.1 to 1000 mg per kilogram body weight per day and most preferably in the range 1 to 5 mg per kilogram body weight per day.

The desired dose is preferably presented as a single dose for daily administration. However, two, three, four, five or six or more sub-doses administered at appropriate intervals throughout the day may also be employed. These sub-doses may be administered in unit dosage forms, for example, containing 0.001 to 100 mg, preferably 0.01 to 10 mg, and most preferably 0.5 to 1.0 mg of active ingredient per unit dosage form, In determining an effective amount or dose, a number of factors are considered by the attending physician, including, but not limited to, the potency and duration of action of the compounds used, the nature and severity of the illness to be treated, as well as the sex, age, weight, general health and individual responsiveness of the patient to be treated, and other relevant circumstances. Those skilled in the art will appreciate that dosages can also be determined with guidance from Goodman & Goldman's The Pharmacological Basis of Therapeutics, Ninth Edition (1996), Appendix II, pp. 1707-1711.

The amount of the compound that can be combined with carrier materials to produce a single dosage form varies depending upon the subject to be treated and the particular mode of administration. For example, a formulation intended for oral administration to humans can contain about 0.5 mg to about 7 g of active agent compounded optionally with an appropriate and convenient amount of carrier material which can vary from about 5 to about 95 percent of the total composition. Dosage unit forms for the compounds of the invention generally contain about 1 mg to about 500 mg of the active ingredient, for example 5 mg, 10 mg, 20 mg, 25 mg, 50 mg, 100 mg, 200 mg, 300 mg, 400 mg, 500 mg, 600 mg, 800 mg or 1000 mg.

The effectiveness of a particular dosage of the compound of the invention can be determined by monitoring the effect of a given dosage on the progression of the disease or its prevention.

(VI) Formulation

The compound of the invention may take any form. It may be synthetic, purified or isolated from natural sources using techniques described in the art.

Illustrative pharmaceutically acceptable salts are prepared from formic, acetic,propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric and galacturonic acids.

Suitable pharmaceutically-acceptable base addition salts include metallic ion salts and organic ion salts. Metallic ion salts include, but are not limited to, appropriate alkali metal (group la) salts, alkaline earth metal (group IIa) salts and other physiologically acceptable metal ions. Such salts can be made from the ions of aluminium, calcium, lithium, magnesium, potassium, sodium and zinc. Organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine(N-methylglucamine) and procaine. All of the above salts can be prepared by those skilled in the art by conventional means from the corresponding compound.

Pharmaceutical compositions can include stabilizers, antioxidants, colorants and diluents. Pharmaceutically acceptable carriers and additives are chosen such that side effects from the pharmaceutical compound are minimized and the performance of the compound is not compromised to such an extent that treatment is ineffective.

The pharmaceutical compositions may be administered enterally and/or parenterally. Oral (intra-gastric) is a typical route of administration. Pharmaceutically acceptable carriers can be in solid dosage forms, including tablets, capsules, pills and granules, which can be prepared with coatings and shells, such as enteric coatings and others well known in the art. Liquid dosage forms for oral administration include pharmaceutically acceptable emulsions, solutions, suspensions, syrups and elixirs.

Parenteral administration includes subcutaneous, intramuscular, intradermal, intravenous, and other routes known in the art. Enteral administration includes solution, tablets, sustained release capsules, enteric coated capsules, and syrups.

When administered, the pharmaceutical composition can be at or near body temperature.

Compositions intended for oral use can be prepared according to any method known in the art for the manufacture of pharmaceutical compositions and such compositions can contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, for example, inert diluents, such as calcium carbonate, sodium carbonate, lactose, calcium phosphate or sodium phosphate, granulating and disintegrating agents, for example, maize starch, or alginic acid, binding agents, for example starch, gelatin or acacia, and lubricating agents, for example magnesium stearate, stearic acid, or talc. Tablets can be uncoated or they can be coated by known techniques, for example to delay disintegration and absorption in the gastrointestinal tract and thereby provide sustained action over a longer period. For example, a time delay material such as glyceryl monostearate or glyceryl distearate can be employed.

Formulations for oral use can also be presented as hard gelatin capsules wherein the active ingredients are mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin or olive oil.

Aqueous suspensions can be produced that contain the active materials in a mixture with excipients suitable for the manufacture of aqueous suspensions. Such excipients include suspending agents, for example, sodium carboxymethylcellulose, methylcellulose, hydroxypropylmethylcellulose, sodium alginate, polyvinylpyrrolidone, gum tragacanth and gum acacia; dispersing or wetting agents can be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyteneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate, Aqueous suspensions can also contain one or more preservatives, for example, ethyl or n-propyl p-hydroxybenzoate, one or more colouring agents, one or more flavouring— agents, or one or more sweetening agents, such as sucrose or saccharin.

Oily suspensions may be formulated by suspending the active ingredients in an omega-3 fatty acid, a vegetable oil, for example, arachis oil, olive oil, sesame oil or coconut oil, or in a mineral oil such as liquid paraffin. The oily suspensions can contain a thickening agent, for example beeswax, hard paraffin or cetyl alcohol.

Sweetening agents, such as those set forth above, and flavouring agents can be added to provide a palatable oral preparation. These compositions can be preserved by addition of an antioxidant such as ascorbic acid.

Dispersible powders and granules suitable for preparation of an aqueous suspension by addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, can also be present.

Syrups and elixirs containing the compound of the invention can be formulated with sweetening agents, for example glycerol, sorbitol, or sucrose. Such formulations can also contain a demulcent, a preservative and flavouring and colouring agents.

The compound of the invention can be administered parenterally, for example subcutaneously, intravenously, or intramuscularly, or by infusion techniques, in the form of sterile injectable aqueous or oleaginous suspensions. Such suspensions can be formulated according to known art using suitable dispersing or wetting agents and suspending agents such as those mentioned above or other acceptable agents. A sterile injectable preparation can be a sterile injectable solution or suspension in a non-toxic parenterally acceptable diluent or solvent, for example a solution in 1,3-butanediol. Among acceptable vehicles and solvents that can be employed are water, Ringer's solution and isotonic sodium chloride solution. In addition, sterile fixed oils are conventionally employed as a solvent or suspending medium. For this purpose, any bland fixed oil may be employed, including synthetic mono- or diglycerides. In addition, omega-3 polyunsaturated fatty acids can find use in preparation of injectables.

Administration can also be by inhalation, in the form of aerosols or solutions for nebulizers, or rectally, in the form of suppositories prepared by mixing the drug with a suitable non-irritating excipient which is solid at ordinary temperature, but liquid at rectal" temperature and will therefore, melt in the rectum to release the drug. Such materials are cocoa butter and polyethylene glycols.

Also encompassed by the present invention is bucca and sub-lingual administration, including administration in the form of lozenges, pastilles or a chewable gum comprising the compounds set forth herein. The compounds can be deposited in a flavoured base, usually sucrose, and acacia or tragacanth.

Other methods for administration of the compounds of the invention include dermal patches that release the medicaments directly into and/or through a subject's skin.

Topical delivery systems are also encompassed by the present invention and include ointments, powders, sprays, creams, jellies, collyriums, solutions or suspensions.

Compositions of the present invention can optionally be supplemented with additional agents such as, for example, viscosity enhancers, preservatives, surfactants and penetration enhancers. Viscosity-building agents include, for example, polyvinyl alcohol, polyvinyl pyrrolidone, methylcellulose, hydroxypropylmethylcellulose, hydroxyethylcellulose, carboxymethylcellulose, hydroxypropylcellulose or other agents known to those skilled in the art. Such agents are typically employed at a level of about 0.01% to about 2% by weight of a pharmaceutical composition.

Preservatives are optionally employed to prevent microbial growth prior to or during use. Suitable preservatives include polyquaternium-1, benzalkonium chloride, thimerosal, chlorobutanol, methylparaben, propylparaben, phenylethyl alcohol, edetate disodium, sorbic acid, or other agents known to those skilled in the art. Typically, such preservatives are employed at a level of about 0.001% to about 1.0% by weight of a pharmaceutical composition.

Solubility of components of the present compositions can be enhanced by a surfactant or other appropriate cosolvent in the composition. Such cosolvents include polysorbates 20, 60 and 80, polyoxyethylene/polyoxypropylene surfactants (e. g., Pluronic F-68, F-84 and P-103), cyclodextrin, or other agents known to those skilled in the art. Typically, such cosolvents are employed at a level of about 0.01% to about 2% by weight of a pharmaceutical composition.

Pharmaceutically acceptable excipients and carriers encompass all the foregoing and the like. The above considerations concerning effective formulations and administration procedures are well known in the art and are described in standard textbooks. See for example Remington: The Science and Practice of Pharmacy, 20th Edition (Lippincott, Williams and Wilkins), 2000; Lieberman et al., ed., Pharmaceutical Dosage Forms, Marcel Decker, New York, N.Y. (1980) and Kibbe et al., ed., Handbook of Pharmaceutical Excipients (3rd Edition), American Pharmaceutical Association, Washington (1999).

Thus, in embodiments where the compound of the invention is formulated together with a pharmaceutically acceptable excipient, any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. The pharmaceutical compositions may take any suitable form, and include for example tablets, elixirs, capsules, solutions, suspensions, powders, granules, nail lacquers, varnishes and veneers, skin patches and aerosols.

The pharmaceutical composition may take the form of a kit of parts, which kit may comprise the composition of the invention together with instructions for use and/or a plurality of different components in unit dosage form.

For oral administration the compound of the invention can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch. Tablets for oral use may include the compound of the invention, either alone or together with pharmaceutically acceptable excipients, such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the compound of the invention is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity.

Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In another embodiment, the compounds of the invention are tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, colouring agents, and flavouring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The compounds of the invention may also be administered parenterally that is, subcutaneously, intravenously, intramuscularly, or interperitoneally. In such embodiments, the compound is provided as injectable doses in a physiologically acceptable diluent together with a pharmaceutical carrier (which can be a sterile liquid or mixture of liquids). Suitable liquids include water, saline, aqueous dextrose and related compound solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as polyethylene-glycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carbomers, methylcellulose, hydroxypropylmethylcellulose, or carboxymethylcellulose), or emulsifying agent and other pharmaceutically adjuvants. Suitable oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil.

Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulphonates, alkyl, olefin, ether, and monoglyceride sulphates, and sutphosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the compound of the invention in solution. Preservatives and buffers may also be used. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of the invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the compound from about 0.1 to about 10% w/v (weight per unit volume).

When used adjunctively, the compounds of the invention may be formulated for use with one or more other drug(s). In particular, the compounds of the invention may be used in combination with analgesics, anti-inflammatories (e.g. steroids), immunomodulatory agents and anti-spasmodics.

Thus, adjunctive use may be reflected in a specific unit dosage designed to be compatible (or to synergize) with the other drug(s), or in formulations in which the compound is admixed with one or more antiinflammatories, cytokines or immunosuppressive agents (or else physically associated with the other drug(s) within a single unit dose). Adjunctive uses may also be reflected in the composition of the pharmaceutical kits of the invention, in which the compound of the invention is co-packaged (e.g. as part of an array of unit doses) with the antimicrobial agents and/or antiinflammatories. Adjunctive use may also be reflected in information and/or instructions relating to the co-administration of the compound with antimicrobial agents and/or antiinflammatories.

(VII) Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

HPLC-UV-MS was performed on a Gilson 321 HPLC with detection performed by a Gilson 170 DAD and a Finnigan AQA mass spectrometer operating in electrospray ionisation mode. The HPLC column used is a Phenomenex Gemini C18 150×4.6 mm or a Phenomenex Gemini C18 50×4.6 mm 3μ. Preparative HPLC was performed on a Gilson 321 with detection performed by a Gilson 170 DAD. Fractions were collected using a Gilson 215 fraction collector. The preparative HPLC column used is a Phenomenex Gemini C18 150×10 mm and the mobile phase is acetonitrile/water.

$^1$H NMR spectra were recorded on a Bruker instrument operating at 300 MHz. NMR spectra were obtained as $CDCl_3$, $CD_3OD$ or DMSO-$d_6$ solutions (reported in ppm), using chloroform as the reference standard (7.26 ppm), methanol (3.35 ppm) or DMSO-$d_6$ (2.50 ppm). When peak multiplicities are reported, the following abbreviations are used s (singlet), d (doublet), t (triplet), m (multiplet), br (broadened), dd (doublet of doublets), dt (doublet of triplets), td (triplet of doublets), obsc. (obscured), app. (apparent). Coupling constants, when given, are reported in Hertz (Hz), Column chromatography was performed either by flash chromatography (40-65 μm silica gel) or using an automated purification system (SP1™ Purification System from Biotageor CombiFlash Companion from ISCO). Reactions in the microwave were performed in an Initiator 8™ (Biotage) or in an Explorer 48 (CEM).

The abbreviations used are DMSO (dimethylsulfoxide), DMF (dimethylformamide), IMS (industrial methylated spirits), IPA (isopropyl alcohol), TLC (thin layer chromatography), Boc (tert-butyloxycarbonyl), RT (retention time), DCM (dichloromethane), TFA (trifluoroacetic acid), LCMS (liquid chromatography-mass spectrometry), NMR (nuclear magnetic resonance), DME (1,2-dimethoxyethane).

MIC data were determined by broth microdilution according to CLSI protocols described in Methods for Antimicrobial Susceptibility Testing of Anaerobic Bacteria; Approved Standard—Seventh Edition [M11-A7, Vol. 27, No 2, January 2007] and Methods for Dilution Antimicrobial Susceptibility Tests for Bacteria That Grow Aerobically; Approved Standard—Seventh Edition [M7-A7, Vol. 26, No 2, January 2006].

Example 1

Preparation of Compounds of General Formula (I)

Method 1

4-(2-(Pyridin-4-yl)-1H-benzo[d]imidazol-5-yl)benzene-1,2-diamine (Intermediate A)

To a stirred solution of 3,3'-diaminobenzidine (3.857 g, 18 mmol) and 4-pyridinecarboxaldehyde (1.41 mL, 15 mmol) in IPA (22.5 mL) and $H_2O$ (7.5 mL), was added sodium metabisulfite (2.852 g, 15 mmol). The suspension was heated to reflux for 16 h. The resulting yellow suspension was poured into water (200 mL) and the precipitate collected through filtration. The yellow solid was triturated with hot methanol and filtered giving intermediate A as an insoluble precipitate (1.672 g, 5.5 mmol, 37%).

LCMS RT=1.05 min, $MH^+$ 302.1; $^1H$ NMR ($d_6$-DMSO): 13.17 (1H, br s), 8.76 (2H, d, J 6.0), 8.09 (2H, d, J 6.0), 7.64 (2H, br s), 7.42 (1H, d, J 8.4), 6.91 (1H, d, J 1.9), 6.77 (1H, dd, J 8.0 and 1.9), 6.60 (1H, d, J 8.0) and 4.58 (4H, br s).

4-(2-(pyridin-3-yl)-1H-benzo[d]imidazol-5-yl)benzene-1,2-diamine (Intermediate B)

To a stirred solution of 3,3'-diaminobenzidine (5.00 g, 23.36 mmol) and 3-pyridinecarboxaldehyde (1.98 mL, 21.02 mmol) in IPA (16 mL) and $H_2O$ (16 mL), was added sodium metabisulfite (4.44 g, 23.36 mmol). The suspension was heated to 160° C. for 15 minutes in the CEM microwave then cooled to room temperature. The resulting yellow suspension was poured into water (150 mL) and the precipitate collected through filtration and dried. The solid was purified by silica column chromatography eluting with neat EtOAc to 9:1 (EtOAc-MeOH) affording intermediate B as a yellow solid (3.92 g, 13.03 mmol, 62%).

LCMS RT=1.44 min, $MH^+$ 302.3; $^1H$ NMR ($d_6$-DMSO): 13.05 (1H, br s), 9.37 (1H, d, J 2.0), 8.69 (1H, dd, J 4.7 and 1,5), 8.51 (1H, dt, J 8.1 and 1.9), 7.70-7.58 (3H, m), 7.41 (1H, dd, J 8.5 and 1.5), 6.93 (1H, d, J 2.0), 6.79 (1H, dd, J 8.0 and 2.0), 6.62 (1H, d, J 8.0) and 4.58 (4H, br s).

2-(2'-(pyridin-4-yl)-1H,1'H-5,5'-bibenzo[d]imidazol-2-yl)thieno[2,3-b]pyridine (Compound 1)

A mixture of 4-(2-(Pyridin-4-yl)-1H-benzo[d]imidazol-5-yl)benzene-1,2-diamine (intermediate A) (50 mg, 0.17 mmol), thieno[2,3-b]pyridine-2-carbaldehyde (33 mg, 0.20 mmol) and $Na_2S_2O_5$ (38 mg. 0.20 mmol) in IPA-$H_2O$ (3:1, 8 mL) was heated under microwave radiation for 170° C. for 10 min. The mixture was absorbed onto silica and purified by column chromatography eluting with (95:5 EtOAc-MeOH to 85:15 EtOAc-MeOH) afforded the title compound as a yellow solid (30 mg, 0.07 mmol, 40%).

LCMS RT=1.38 min, $MH^+$ 445.1; $^1H$ NMR (MeOD): 8.74 (2H, dd, J 4.7 and 1.6), 8.58 (1H, dd, J 4.7 and 1.6), 8.31 (1H, dd, J 8.1 and 1.6), 8.10 (2H, dd, J 4.7 and 1.6), 7.78 (1H, s), 7.90-7.62 (6H, m) and 7.48 (1H, dd, J 8.1 and 4.7).

The following compounds were prepared in a similar manner using the relevant intermediate and purifying by crystallization or column chromatography where necessary:

2-(Benzo[b]thiophen-2-yl)-2'-(pyridin-4-yl)-1H,1'H-5,5'-bibenzo[d]imidazoleidole (Compound 2)

LCMS RT=1.51 min, $MH^+$ 444.2; $^1H$ NMR(MeOD): 8.64 (2H, m), 8.01 (2H, 7.93 (1H, m), 7.79-7.89 (3H, m), 7.51-7.78 (5H, m), 7.34 (2H, m).

2-(benzofuran-5-yl)-2'-(pyridin-4-yl)-1H,1'H-5,5'-bibenzo[d]imidazole (Compound 3)

LCMS RT=1.23 min, $MH^+$ 428.1; $^1H$ NMR (MeOD): 8.76 (2H, dd, J 4.7 and 1.6), 8.40 (1H, d, J 1.6), 8.15-8.08 (3H, m), 8.00-7.60 (8H, m) and 7.02 (1H, dd, J 2.2 and 0.9).

6-(2'-(pyridin-4-yl)-1H, 3'H-5,5'-bibenzo[d]imidazol-2-yl)benzo[d]imidazole (Compound 4)

LCMS RT=1.09 min, $MH^+$ 428.5; $^1H$ NMR (MeOD): 8.75 (2H, dd, J 4.6 and 1.7), 8.42 (1H, bs), 8.32 (1H, s), 8.12 (2H, dd, J 4.6 and 1.7), 8.07-7.71 (7H, m) and 7.62 (1H, dd, J 8.4 and 1.7).

2-(benzo[b]thiophen-5-yl)-2'-(pyridin-4-yl)-1H,3'H-5,5'-bibenzo[d]imidazole (Compound 5)

LCMS RT=1.26 min, $MH^+$ 444.2; $^1H$ NMR (MeOD): 8.65 (2H, dd, J 4.6 and 1.7), 8.49 (1H, t, J 1.1), 8.01-7.99 (4H, m), 7.78-7.51 (7H, m) and 7.43 (1H, d, J 5.5).

2-(1H-indol-5-yl)-2'-(pyridin-4-yl)-1H,3'H-5,5'-bibenzo[d]imidazole (Compound 6)

LCMS RT=1.16 min, $MH^+$ 427.3; $^1H$ NMR (MeOD): 8.64 (2H, dd, J 4.6 and 1.7), 8.25 (1H, d, J 1.1), 8.01 (2H, dd, J 4.6 and 1.7), 7.83-7.43 (6H, m), 7.50-7.43 (2H, m) 7.25 (1H, d, J 3.2) and 6.51 (1H, dd, J 3.2 and 0.8).

2-(2,3-Dihydrobenzofuran-5-yl)-2'-(pyridin-4-yl)-1H,3'H-5,5'-bibenzo[d]imidazole (Compound 7)

LCMS: RT=1.21 min, $MH^+$ 430.1; $^1H$ NMR ($d_6$-DMSO): 8.76 (2H, dd, J 4.6 and 1.6), 8.09 (2H, dd, J 4.6 and 1.6), 8.03 (1H, s), 7.92 (2H, dd, J 8.2 and 1.8), 7.84-7.52 (5H, m), 6.93 (1H, d, J 8.3), 4.62 (2H, t, J 8.7) and 3.28 (2H, t, J 8.8).

2-(imidazo[1,2-a]pyridin-6-yl)-2'-(pyridin-4-yl)-1H, 1'H-5,5'-bibenzo[d]imidazole (Compound 8)

LCMS: RT=1.11 min, 428.1 $MH^+$; $^1H$ NMR (MeOD): 9.18 (1H, s), 8.76 (2H, dd, J4.6 and 1.6), 8.12 (2H, dd, J 4.6 and 1.6), 8.04 (1H, s), 8.00 (1H, dd, J 9.4 and 1.7) and 7.95-7.64 (8H, m).

2-(benzo[d][1,3]dioxol-5-yl)-2'-(pyrdinin-4-yl)-1H,1'H-5,5'-bibenzo[d]imidazole (Compound 9)

LCMS: RT=1.23 min, MH+ 431.8; $^1$H NMR (MeOD): 8.76 (2H, dd, J 4.7 and 1.6), 8.13 (2H, dd, J 4.6 and 1.6), 7.93-7.61 (8H, m), 7.02 (1H, d, J 8.1) and 6.09 (2H, s).

2-(benzofuran-2-yl)-2'-(pyridin-4-yl)-1H,1'H-5,5'-bibenzo[d]imidazole (Compound 10)

LCMS: RT=1.48 min, MH+ 428.5; $^1$H NMR (MeOD): 8.64 (2H, dd, J 4.6 and 1.7), 8.00 (2H, dd, J 4.6 and 1.7) and 7.79 (2H, m), 7.65-7.52 (6H, m), 7.49 (1H, d, J 0.9) 7.33 (1H, dt, J 7.3 and 1.3), 7.23 (1H, dt, J 7.5 and 1.0).

2-(2'-(pyridin-4-yl)-1H,1'H-[5,5'-bibenzo[d]imidazol]-2-yl)thieno[2,3-c]pyridine (Compound 11)

LCMS: RT=1.36 min, MH+ 445.2; $^1$H NMR (MeOD): 9.14 (1H, s), 8.70 (2H, d, J 5.4), 8.41 (1H, d, J 5.5), 8.05 (2H, d, J 5.5), 7.98 (1H, s) and 7.91-7.55 (7H, m)

2-(imidazo[1,2-a]pyridin-6-yl)-2'-(pyridin-3-yl)-1H,1'H-5,5'-bibenzo[d]imidazole (Compound 12)

LCMS: RT=1.80 min, MH+ 428.7; $^1$H NMR (d$_6$-DMSO): 13.26 (2H, br s), 9.52 (1H, s), 9.45 (1H, d, J 2.0), 8.76 (1H, dd, J 4.8 and 1.5), 8.60 (1H, dt, J 8.0 and 1.8), 8.20 (1H, s), 8.07 (1H, dd, J 9.4 and 1.7), 7.95 (2H, d, J 7.0), 7.85-7.73 (4H, m) and 7.70-7.63 (3H, m)

2-(2'-(pyridin-3-yl)-1H,1'H-[5,5'-bibenzo[d]imidazol]-2-yl)thieno[2,3-b]pyridine (Compound 13)

LCMS: RT=2.33 min, MH+ 446.1; $^1$H NMR (d$_6$-DMSO): 13.33 (2H, br s), 9.39 (1H, d, J 2.2), 8.70 (1H, dd, J 4.8 and 1.6), 8.63 (1H, dd, J 4.6 and 3.0), 8.54 (1H, dt, J 8.0 and 2.0), 8.41 (1H, dd, J 8.0 and 1.6), 8.17 (1H, s), 8.07-7.69 (4H, m), 7.69-7.58 (3H, m) and 7.52 (1H, dd, J 8.0 and 4.6)

Example 2

Activity of the Compounds of the Invention

A list of preferred compounds of general formula (I) together with their minimum inhibitory concentration (MIC) against *Clostridium difficile* ATCC700057 and a panel of gut flora indicator bacteria is summarized in Table 2 (below).

TABLE 2

| Example | Name | C. difficile | B. fragilis | E. coli | L. paracasei | B. dentium | B. adolescentis | S. aureus | E. faecalis |
|---|---|---|---|---|---|---|---|---|---|
| 1 | 2-(2'-(pyridin-4-yl)-1H,1'H-5-5'-bibenzo[d]imidazol-2-yl)thieno[2,3-b]pyridine | ++++ | + | + | + | + | ++ | + | + |
| 2 | 2-(benzo[b]thiophen-2-yl)-2'-(pyridin-4-yl)-1H,1'H-5,5'-bibenzo[d]imidazole | +++ | + | + | + | + | + | + | + |
| 3 | 2-(benzofuran-5-yl)-2'-(pyridin-4-yl)-1H,1'H-5,5'-bibenzo[d]imidazole | ++++ | + | + | ++ | ++ | +++ | ++++ | ++++ |
| 4 | 6-(2'-(pyridin-4-yl)-1H,3'H-5,5'-bibenzo[d]imidazol-2-yl)benzo[d]imidazole | ++++ | + | + | + | + | + | + | + |
| 5 | 2-(benzo[b]thiophen-5-yl)-2'-(pyridin-4-yl)-1H,3'H-5,5'-bibenzo[d]imidazole | ++++ | + | + | + | + | ++ | + | ++ |
| 6 | 2-(1H-indol-5-yl)-2'-(pyridin-4-yl)-1H,3'H-5,5'-bibenzo[d]imidazole | ++++ | + | + | + | + | ++ | ++ | + |
| 7 | 2-(2,3-dihydrobenzofuran-5-yl)-2'-(pyridin-4-yl)-1H,3'H-5,5'-bibenzo[d]imidazole | ++++ | + | + | + | + | +++ | + | +++ |
| 8 | 2-(imidazo[1,2-a]pyridin-6-yl)-2'-(pyridin-4-yl)-1H,1'H-5,5'-bibenzo[d]imidazole | ++++ | + | + | + | + | + | + | + |
| 9 | 2-(benzo[d][1,3]dioxol-5-yl)-2'-(pyridin-4-yl)-1H,1'H-5,5'-bibenzo[d]imidazole | ++++ | + | + | + | + | + | + | + |
| 10 | 2-(benzofuran-2-yl)-2'-(pyridin-4-yl)-1H,1'H-5,5'-bibenzo[d]imidazole | ++++ | + | + | + | + | ++ | ++ | + |
| 11 | 2-(2'-(pyridin-4-yl)-1H,1'H-[5,5'-bibenzo[d]imidazol]-2-yl)thieno[2,3-c]pyridine | ++++ | + | + | + | + | + | + | + |
| 12 | 2-(imidazo[1,2-a]pyridin-6-yl)-2'-(pyridin-3-yl)-1H,1'H-5,5'-bibenzo[d]imidazole | ++++ | + | + | + | + | + | + | + |
| 13 | 2-(2'-(pyridin-3-yl)-1H,1'H-[5,5'-bibenzo[d]imidazol]-2-yl)thieno[2,3-b]pyridine | ++++ | + | + | + | + | + | + | + |

In the above table, the symbols used to indicate the MIC values are:
MIC ≤ 1 µg/ml = ++++
MIC ≤ 4 µg/ml = +++
MIC ≤ 32 µg/ml = ++
MIC ≥ 64 µg/ml = +

The bacterial strains used were:
*Bacteroides fragilis* ATCC 25285
*Escherichia coli* ATCC25922
*Lactobacillus paracasei* Z1 83
*Bifidobacterium dentium* NCTC 1181
*B. adolescentis* MWR144
*Staphylococcus aureus* ATCC29213
*Enterococcus faecalis* ATCC29212

The indicator strains are representatives of the normal gut flora and therefore act as surrogates for the microbial gut flora. Thus, the data show that the compounds of the invention are selective *Clostridium difficile* agents (as hereinbefore defined) which exhibit bacteriostatic and/or bacteriocidal activity against *C. difficile* but which spare the normal gut flora. The compounds of the invention therefore find utility in the treatment of CDAD without causing pathological disturbance of the normal gut flora.

(VIII) Equivalents

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A compound of formula (I):

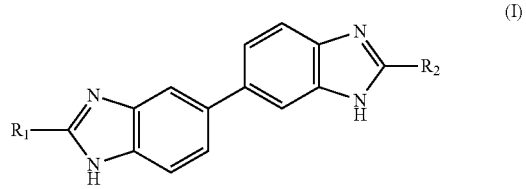

(I)

$R^1$ is selected from the group consisting of an optionally substituted pyridyl group and an optionally substituted thiazole group, the optional substitution being with one or more substituents selected from the group consisting of halo, CN, $NO_2$, $R^3$, $OR^3$, $N(R^3)_2$, $COR^3$, $CO_2R^3$, $C(=O)SR^3$, $SR^3$, $S(=O)R^3$, $SO_2R^3$, $NR^4C(=O)R^3$, $NR^4CO_2R^3$, $OC(=O)NR^3R^4$, $NR^4SO_2R^3$, $C(=NR^4)NR^3R^4$, $C(=S)NR^3R^4$, $NR^4C(=NR^4)NR^3R^4$, $NR^4C(=S)NR^3R^4$, $NR^4C(=O)NR^3R^4$, $CONR^3R^4$ and $SO_2NR^3R^4$;

$R^2$ is an optionally substituted aromatic 8-14 membered fused bicyclic or tricyclic ring system in which one or more of the carbon atoms may be replaced by N, O, S, SO or $SO_2$ and the optional substitution being with one or more substituents selected from the group consisting of halo, CN, $NO_2$, $R^3$, $OR^3$, $N(R^3)_2$, $COR^3$, $CO_2R^3$, $C(=O)SR^3$, $SR^3$, $S(=O)R^3$, $SO_2R^3$, $NR^4C(=O)R^3$, $NR^4CO_2R^3$, $OC(=O)NR^3R^4$, $NR^4SO_2R^3$, $C(=NR^4)NR^3R^4$, $C(=S)NR^3R^4$, $NR^4C(=NR^4)NR^3R^4$, $NR^4C(=S)NR^3R^4$, $NR^4C(=O)NR^3R^4$, $CONR^3R^4$ and $SO_2NR^3R^4$;

$R^3$ is selected from the group consisting of H, $C_1$-$C_6$ alkyl, $C_2$-$C_6$ alkenyl, $C_2$-$C_6$ alkynyl, $C_3$-$C_7$ carbocyclyl, $C_4$-$C_7$ heterocyclyl and 5- or 6-membered aryl or heteroaryl, any of which may be optionally substituted with one or more substituents selected from the group consisting of halo, CN, $NO_2$, $R^4$, $OR^4$, $N(R^4)_2$, $COR^4$, $CO_2R^4$, $C(=O)SR^4$, $SR^4$, $S(=O)R^4$, $SO_2R^4$, $NR^4C(=O)R^4$, $NR^4CO_2R^4$, $OC(=O)NR^4)_2$, $NR^4SO_2R^4$, $C(=NR^4)N(R^4)_2$, $C(=S)N(R^4)_2$, $NR^4C(=NR^4)N(R^4)_2$, $NR^4C(=S)N(R^4)_2$, $NR^4C(=O)N(R^4)_2$, $CON(R^4)_2$ and $SO_2N(R^4)_2$;

$R^4$ is selected from the group consisting of hydrogen, $C_1$-$C_6$ alkyl and $C_3$-$C_7$ carbocyclyl, optionally substituted with one or more halo atoms;

or a pharmaceutically acceptable N-oxide, salt, hydrate, solvate, complex, bioisostere, or metabolite thereof.

2. The compound of claim 1 wherein $R^2$ is an optionally substituted aromatic 8-10 membered fused bicyclic ring system in which one or more of the carbon atoms may be replaced by N, O, S, SO or $SO_2$ and the optional substitution being with one or more substituents selected from the group consisting of halo, CN, $NO_2$, $R^3$, $OR^3$, $N(R^3)_2$, $COR^3$, $CO_2R^3$, $C(=O)SR^3$, $SR^3$, $S(=O)R^3$, $SO_2R^3$, $NR^4C(=O)R^3$, $NR^4CO_2R^3$, $OC(=O)NR^3R^4$, $NR^4SO_2R^3$, $C(=NR^4)NR^3R^4$, $C(=S)NR^3R^4$, $NR^4C(=NR^4)NR^3R^4$, $NR^4C(=S)NR^3R^4$, $NR^4C(=O)NR^3R^4$, $CONR^3R^4$ and $SO_2NR^3R^4$.

3. The compound of claim 2 wherein $R^2$ is an optionally substituted aromatic 9-membered bicyclic ring system in which one or more of the carbon atoms may be replaced by N, O, S, SO or $SO_2$ and the optional substitution being with one or more substituents selected from the group consisting of halo, CN, $NO_2$, $R^3$, $OR^3$, $N(R^3)_2$, $COR^3$, $CO_2R^3$, $C(=O)SR^3$, $SR^3$, $S(=O)R^3$, $SO_2R^3$, $NR^4C(=O)R^3$, $NR^4CO_2R^3$, $OC(=O)NR^3R^4$, $NR^4SO_2R^3$, $C(=NR^4)NR^3R^4$, $C(=S)NR^3R^4$, $NR^4C(=NR^4)NR^3R^4$, $NR^4C(=S)NR^3R^4$, $NR^4C(=O)NR^3R^4$, $CONR^3R^4$ and $SO_2NR^3R^4$.

4. The compound of claim 1 wherein $R^2$ is an optionally substituted aromatic fused 5,6-membered bicyclic ring system.

5. The compound of claim 4 wherein $R^2$ is:
(a) an optionally substituted thienopyridyl group; or
(b) an optionally substituted benzothiophene group; or
(c) an optionally substituted benzofuran group; or
(d) an optionally substituted pyridyl imidazole group; or
(e) an optionally substituted benzodioxol group; or
(f) an optionally substituted indole group.

6. The compound of claim 1 wherein $R^2$ is an optionally substituted aromatic fused 6,6-membered bicyclic ring system.

7. The compound of claim 6 wherein $R^2$ is:
(a) an optionally substituted isoquinolone group; or
(b) an optionally substituted quinoxaline group; or
(c) an optionally substituted isoquinoline group; or
(d) an optionally substituted quinoline group; or
(e) an optionally substituted naphthyridine group.

8. The compound of claim 1 wherein $R^1$ and $R^2$ are the same.

9. The compound of claim 1 wherein $R^1$ and $R^2$ are different.

10. The compound of claim 1, wherein the compound is selected from the group consisting of:
2-(2'-(pyridin-4-yl)-1H,1'H-5,5'-bibenzo[d]imidazol-2-yl)thieno[2,3-b]pyridine,
2-(benzo[b]thiophen-2-yl)-2'-(pyridin-4-yl)-1H,1'H-5,5'-bibenzo[d]imidazole,
2-(benzofuran-5-yl)-2'-(pyridin-4-yl)-1H,1'H-5,5'-bibenzo[d]imidazole,
6-(2'-(pyridin-4-yl)-1H,3'H-5,5'-bibenzo[d]imidazol-2-yl)benzo[d]imidazole,
2-(benzo[b]thiophen-5-yl)-2'-(pyridin-4-yl)-1H,3'H-5,5'-bibenzo[d]imidazole,
2-(1H-indol-5-yl)-2'-(pyridin-4-yl)-1H,3'H-5,5'-bibenzo[d]imidazole, 2-(2,3-dihydrobenzofuran-5-yl)-2'-(pyridin-4-yl)-1H,3'H-5,5'-bibenzo[d]imidazole,
2-(imidazo[1,2-a]pyridin-6-yl)-2'-(pyridin-4-yl)-1H,1'H-5,5'-bibenzo[d]imidazole,
2-(benzo[d][1,3]-dioxol-5-yl)-2'-(pyridin-4-yl)-1H,1'H-5,5'-bibenzo[d]imidazole,
2-(benzofuran-2-yl)-2'-(pyridin-4-yl)-1H,1'H-5,5'-bibenzo[d]imidazole,
2-(2'-(pyridin-4-yl)-1H,1'H-[5,5'-bibenzo[d]imidazol]-2-yl)thieno[2,3-c]pyridine,
2-(imidazo[1,2-a]pyridin-6-yl)-2'-(pyridin-3-yl)-1H,1'H-5,5'-bibenzo[d]imidazole, and
2-(2'-(pyridin-3-yl)-1H,1'H-[5,5'-bibenzo[d]imidazol]-2-yl)thieno[2,3-b]pyridine,
and pharmaceutically acceptable N-oxides, salts, hydrates, solvates, complexes, bioisosteres, and metabolites thereof.

11. The compound of claim 1, wherein the compound is 2-(imidazo[1,2-a]pyridin-6-yl)-2'-(pyridin-4-yl)-1H,1'H-5,5'-bibenzo[d]imidazole,
or a pharmaceutically acceptable N-oxide, salt, hydrate, solvate, complex, bioisostere, or metabolite thereof.

12. A combination comprising a compound as defined in claim 1, or a pharmaceutically acceptable N-oxide, salt, hydrate, solvate, complex, bioisostere, or metabolite thereof, and an adjunctive agent selected from the group consisting of:
(a) vancomycin;
(b) metronidazole;
(c) a probiotic;
(d) a pre-biotic;
(e) a bacteriotoxin sequestrant;
(f) intravenous immunoglobulin; and
(g) an anti-diarrhoeal agent.

13. The combination of claim 12 further comprising probiotic selected from the group consisting of *Saccharomyces* spp. and *Lactobacillus* spp.

14. The combination of claim 12 wherein the compound and adjunctive agent are physically or non-physically associated.

15. A pharmaceutical composition comprising a compound as defined in claim 1 or a pharmaceutically acceptable N-oxide, salt, hydrate, solvate, complex, bioisostere, or metabolite thereof, and a pharmaceutically acceptable carrier.

* * * * *